(12) United States Patent
Ben Shabat et al.

(10) Patent No.: US 8,716,334 B2
(45) Date of Patent: May 6, 2014

(54) SUBSTITUTED CYCLOHEXYLIDENE-ETHYLIDENE-OCTAHYDRO-INDENE COMPOUNDS

(75) Inventors: Shimon Ben Shabat, Jerusalem (IL); Amnou Sintov, Omer (IL)

(73) Assignee: Ben Gurion University of the Negev Research and Development Authority, Beer Sheva (IL)

( * ) Notice: Subject to any disclaimer, the term of this patent is extended or adjusted under 35 U.S.C. 154(b) by 233 days.

(21) Appl. No.: 12/993,262

(22) PCT Filed: Jun. 16, 2009

(86) PCT No.: PCT/IL2009/000597
§ 371 (c)(1),
(2), (4) Date: Nov. 18, 2010

(87) PCT Pub. No.: WO2009/153782
PCT Pub. Date: Dec. 23, 2009

(65) Prior Publication Data
US 2011/0098350 A1    Apr. 28, 2011

Related U.S. Application Data

(60) Provisional application No. 61/129,290, filed on Jun. 17, 2008.

(51) Int. Cl.
*A61K 31/336* (2006.01)
*C07D 317/02* (2006.01)
*C07D 303/32* (2006.01)

(52) U.S. Cl.
USPC ........... 514/467; 514/475; 549/453; 549/548; 549/554

(58) Field of Classification Search
USPC .................. 549/453, 548, 554; 514/467, 475
See application file for complete search history.

(56) References Cited

U.S. PATENT DOCUMENTS

| 4,866,048 | A | | 9/1989 | Calverley et al. | |
|---|---|---|---|---|---|
| 6,100,294 | A | * | 8/2000 | Reddy | 514/451 |
| 2006/0286054 | A1 | | 12/2006 | Gomez | |
| 2007/0135395 | A1 | | 6/2007 | Hansen et al. | |

OTHER PUBLICATIONS

Calverley, 1988, Vitam. D: Mol., Cell. Clin. Endocrinol., p. 51-52.*
Masuda, 1994, Journal of Biological Chemistry, vol. 269(7), p. 4794-4803.*
Golub et al, 1999, Science, vol. 286, p. 531-537.*
Targeted Cancer Therapies, http://www.cancer.gov/cancertopics/factsheet/therapy/targeted, accessed Jun. 21, 2010.*
Cancer Prevention Overview, http://www.cancer.gov/cancertopics/pdq/prevention/overview/patient, accessed Nov. 14, 2012.*
Voskoglou-Nomiko et al, 2003, Clinical Cancer Research, vol. 9, p. 4227-4239.*
Masuda et al, 2006, Mol Cancer Ther, vol. 5, p. 797-808.*
Tremezaygues et al, 2011, Dermato-Endocrinology, vol. 3, No. 3, p. 180-186.*
Holick, Clin J Am Soc Nephrol, 2008, vol. 3, p. 1548-1554.*
Beer et al.; "Calcitriol in cancer treatment: from the lab to the clinic", Mol Cancer Ther 3:373-381 (2004).
Berkovich et al.; "Induction of apoptosis and inhibition of prostate and breast cancer growth by BGP-15, a new calcipotriene-derived vitamin D3 analog", Anticancer Drugs 21(6):609-618 (2010).
Binderup et al.; "Effects of a novel vitamin D analogue MC903 on cell proliferation and differentiation in vitro and on calcium metabolism in vivo", Biochem Pharmacol 37:889-895 (1988).
Bouillon et al.; Structure-function relationships in the vitamin D endocrine system. Endocr Rev 1995; 16:200-257.
Brown et al.; "Vitamin D", Am J Physiol 277:F157-F175 (1999).
Calverley; "Synthesis of Biologically Active Cyclopropane Analogues of 1α,25-Dihydroxy- and 1α-Hydroxy-Vitamin $D_3$", Proc $7^{th}$ Workshop on Vitamin D, Norman et al Editors, Apr. 1988, pp. 51-52.
Carlberg; "Ligand-mediated conformational changes of the VDR are required for gene transactivation", J Steroid Biochem Mol Biol 89-90:227-232 (2004).
Chambers et al.; "The permeability of normal, adenomatous, ulcerative colitic and malignant large bowel epithelial cell membranes to inulin", Br J Exp Path 66:309-315 (1985).
Chung et al.; "Role of Vitamin D receptor in the antiproliferative effects of calcitriol in tumor-derived endothelial cells and tumor angiogenesis in vivo", Cancer Res 69:967-975 (2009).
Grzywacz et al.; "Methyl substitution of the 25-hydroxy group on 2-methylene-19-nor-1a,25-dihydroxyvitamin D3 (2MD) reduces potency but allows bone selectivity", Arch Biochem Biophys 2007; 460:274-284.
Guzey et al.; "Apoptosis induction by 1alpha,25-dihydroxyvitamin D3 in prostate cancer", Mol Cancer Ther 1:667-677 (2002).
Hansen et al.; "1 alpha, 25-Dihydroxyvitamin D3 inhibits the invasive potential of human breast cancer cells in vitro", Clin Exp Metastasis 12:195-202 (1994).
Hisatake et al.; "5 6-trans-16-ene-Vitamin D3: a new class of potent inhibitors of proliferation of prostate breast and myeloid leukemic cells", Cancer Res 1999; 59:4023-4029.
Hussain-Hakimjee et al.; "Regulation of steroid receptor expression by 1alpha-hydroxyvitamin D3 in hormoneresponsive breast cancer cells", Anticancer Res 29:3555-3561 (2009).
Inaba et al.; "Effect of substituting fluorine for hydrogen at C-26 and C-27 on the side chain of 1,25-dihydroxyvitamin D3", Biochem Pharmacol 1993; 45:2331-2336.

(Continued)

*Primary Examiner* — Rebecca Anderson
*Assistant Examiner* — Karen Cheng
(74) *Attorney, Agent, or Firm* — Pearl Cohen Zedek Latzer Baratz LLP; Mark S. Cohen

(57) ABSTRACT

Novel substituted cyclohexylidene-ethylidene-octahydro-indene compounds and compositions comprising the same are described. The compounds exhibit profound anti-proliferative effects, in comparison to other compounds known for their anti-cancer and anti-hyperproliferative ability. Methods of use of such compounds and compositions are described for treating a variety of cancers, inflammatory and other hyperproliferative diseases and disorders.

20 Claims, 16 Drawing Sheets

(56) References Cited

OTHER PUBLICATIONS

International Search Report for PCT Application No. PCT/IL2009/000597 mailed Oct. 13, 2009.

James et al.; "Effects of 1,25 dihydroxyvitamin D3 and its analogues on induction of apoptosis in breast cancer cells", J Steroid Biochem Mol Biol 58:395-401 (1996).

Jones; "Pharmacokinetics of vitamin D toxicity", Am J Clin Nutr 2008; 88:582S-586S.

Lokeshwar et al.; "Inhibition of prostate cancer metastasis in vivo: a comparison of 1,23-dihydroxyvitamin D (calcitriol) and EB1089", Cancer Epidemiol Biomarkers Prev 8:241-248 (1999).

Luba et al.; "Chronic plaque psoriasis". Am Fam Physician 73:636-644 (2006).

Luo et al.; "Bid a Bcl2 interacting protein mediates cytochrome c release from mitochondria in response to activation of cell surface death receptors", Cell 1998; 94:481-490.

Mangelsdorf et al.; "The nuclear receptor superfamily: the second decade", Cell 83(6):835-839 (1995).

Masuda et al.; "In vitro metabolism of the anti-psoriatic vitamin D analog, calcipotriol, in two cultured human keratinocyte models", J Biol Chem 269(7):4794-4803 (1994).

Norman et al.; "Structure-function studies on analogues of 1a,25-dihydroxyvitamin D3: differential effects on leukemic cell growth differentiation and intestinal calcium absorption", Cancer Res 1990; 50:6857-6864.

Ohno et al.; "Fluorinated vitamin D analogs to probe the conformation of vitamin D in its receptor complex: 19F-NMR studies and biological activity", Chem Pharm Bull 2002; 50:475-483.

Peleg et al.; "Low-calcemic highly antiproliferative 1-difluoromethyl hybrid analogs of the natural hormone 1a,25-dihydroxyvitamin D3: design synthesis and preliminary biological evaluation", J Med Chem 2006; 49:7513-7517.

Posner et al.; "Conceptually new low-calcemic oxime analogues of the hormone 1a,25-dihydroxyvitamin D3:synthesis and biological testing", J Med Chem 2002; 45:1723-1730.

Posner et al.; "Difluoromethyl analogs of the natural hormone 1a,25-dihydroxyvitamin D3: design synthesis and preliminary biological evaluation", J Steroid Biochem Mol Biol 2007; 103:213-221.

Posner et al.; "Highly antiproliferative low-calcemic side-chain ketone analogs of the hormone 1a,25-dihydroxyvitamin D3", Bioorg Med Chem 2005; 13:5569-5580.

Posner et al.; "Low-calcemic efficacious 1a,25-dihydroxyvitamin D3 analog QW-1624F2-2: calcemic dose-response determination preclinical genotoxicity testing and revision of A-ring stereochemistry", Steroids 2004; 69:757-762.

Reichrath et al.; "Biologic effects of topical calcipotriol (MC 903) treatment in psoriatic skin", J Am Acad Dermatol 36:19-28 (1997).

Schwartz et al.; "1 alpha,25-Dihydroxyvitamin D (calcitriol) inhibits the invasiveness of human prostate cancer cells", Cancer Epidemiol Biomarkers Prev 6:727-732 (1997).

Sintov et al.; "Inhibition of cancer growth and induction of apoptosis by BGP-13 and BGP-15, new calcipotriene-derived vitamin D3 analogs, in-vitro and in-vivo studies", Invest New Drugs (2013) 31:247-255.

Takahashi et al.; "Similarly potent action of 1,25-dihydroxyvitamin D3 and its analogues, tacalcitol, calcipotriol, and maxacalcitol, on normal human keratinocyte proliferation and differentiation", J Dermatol Sci 31:21-28 (2003).

Trump et al.; "Anti-tumor activity of calcitriol: pre-clinical and clinical studies", J Steroid Biochem Mol Biol 89-90:519-526 (2004).

Usera et al.; "Antiproliferative low-calcemic fluorinated sulfone analogs of 1a,25-dihydroxyvitamin D3: chemical synthesis and biological evaluation", Bioorg Med Chem 2007; 15:5509-5518.

Wang et al.; "Cyclin-dependent kinase inhibitor p27 as a mediator of the G1-S phase block induced by 1,25-dihydroxyvitamin D3 in HL60 cells", Cancer Res 1996; 56:264-267.

Wiese et al.; "Up-regulation of the vitamin D receptor in response to 1,25-dihydroxyvitamin D3 results from ligand-induced stabilization", J Biol Chem 267:20082-20086 (1992).

Wietrzyk et al.; "Antitumor properties of diastereomeric and geometric analogs of vitamin D3", Anticancer Drugs 18:447-457 (2007).

Young et al. "Treating tumor-bearing mice with vitamin D3 diminishes tumorinduced myelopoiesis and associated immunosuppression, and reduces tumor metastasis and recurrence", Cancer Immunol Immunother 41:37-45 (1995).

Zhuang et al.; "Antiproliferative effect of 1 alpha, 25-dihydroxyvitamin D3 in human prostate cancer cell lineLNCaP involves reduction of cyclin-dependent kinase 2 activity and persistent G1 accumulation", Endocrinology 139:1197-1207 (1998).

* cited by examiner

\* p<0.001 relative to vitamin $D_3$
\*\* p<0.001 relative to CPT.

MCF-7    5 µmol/L

LNCaP    1 µmol/L

MCF-7    1 µmol/L

SUBSTITUTED CYCLOHEXYLIDENE-ETHYLIDENE-OCTAHYDRO-INDENE COMPOUNDS

CROSS-REFERENCE TO RELATED APPLICATIONS

This application is a National Phase Application of PCT International Application No. PCT/IL2009/000597, International Filing Date Jun. 16, 2009, claiming priority of U.S. Provisional Application Ser. No. 61/129,290 filed Jun. 17, 2008.

FIELD OF THE INVENTION

The invention provides calcipotriol derivatives, composition comprising at least one calcipotriol derivative, and methods of using the same.

BACKGROUND OF THE INVENTION

Vitamin $D_3$ analogs are useful for the treatment of hyperproliferative skin diseases, such as psoriasis vulgaris and are involved in essential cell regulatory processes such as proliferation and differentiation in a number of different cell types including cancer cells. The vitamin $D_3$ analog calcitriol has been shown to induce cell growth arrest and to possess differentiation-inducing behavior in both primary melanocytes and melanoma cell lines. It was shown that growth inhibitory effects of calcitriol are mediated by increased levels of p21 in the prostatic carcinoma cell lines. There has also been intense interest in effects of calcitriol on apoptosis, malignant cell invasion and metastasis. It is recognized that calcitriol induces several biological effects influencing a number of signal transduction pathways, and may lead to severe side effects. These biological effects make vitamin D analogs promising candidate agents for cancer therapy. However, the therapeutic efficacy of systemically applied vitamin D analogs for treating cancer has not yet fulfilled its promise. One main reason for these disappointing results is that the use of systemically applied vitamin D analogs is limited by severe side effects, mostly hypercalcemia, at the supraphysiological doses needed to reach clinical improvement.

Calcipotriol is a synthetic derivative of calcitriol and it is used in the treatment of psoriasis. The precise mechanism of calcipotriol in remitting psoriasis is not well-understood. The efficacy of calcipotriol, a vitamin $D_3$ analog, in inhibition of proliferation in a variety of cell types, and its therapeutic potential in the topical treatment of psoriasis has been established in a large number of clinical trials. In vitro studies have shown that calcipotriol stimulates terminal cell differentiation and has antiproliferative effects. In vivo, calcipotriol has been shown to reduce the number of cycling epidermal cells. These properties make calcipotriol an ideal candidate for the topical treatment of hyperproliferative disorders. While it has been approved for topical use in psoriasis, its potential for use in other disorders has not yet been fully investigated.

SUMMARY OF THE INVENTION

In one embodiment, this invention provides a compound of formula I:

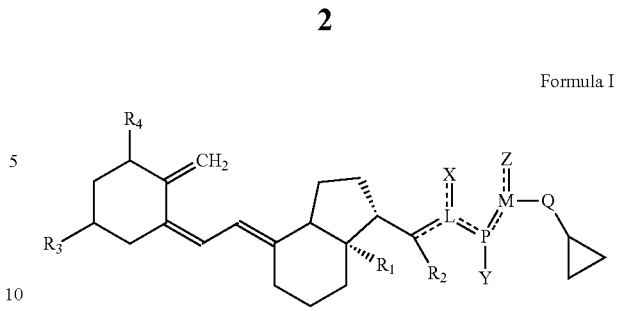

Formula I wherein $R_1$ and $R_2$ are independently H, $C_{(1-4)}$ alkyl, halogen, cycloalkyl;

$R_3$ and $R_4$ are independently OH, OAlk, Alk denoting a $C_{(1-4)}$ alkyl group, halogen, CN, $NH_2$, $NO_2$, $C_{(1-4)}$ alkylene, haloalkyl.

wherein:

L is carbon and optionally forms a double bond with P or with X, or L forms an epoxide with P.

P is carbon and optionally forms a double bond with L or M, or P forms an epoxide with L or M or P is O;

Q is nothing, or a carbonyl;

M is an alkylene (C1-C4), or optionally a carbon which forms a double bond with P, or M forms an epoxide with P.

Y is nothing, H, OH, OAlk, Alk denoting a $C_{(1-4)}$ alkyl group, O—CO-alkyl.

X is H, oxo, OH, or halogen, OAlk, Alk denoting a $C_{(1-4)}$ alkyl group, O—CO-alkyl.

Z is H, oxo, OH or halogen, OAlk, Alk denoting a $C_{(1-4)}$ alkyl group, O—CO-alkyl.

Or L, P, M, Z and X forms a saturated or unsaturated 5-7 membered, carbocyclic or heterocyclic ring, wherein L, P, M are defined as above and X and Z are independently O, N, S or C.

In one embodiment, a compound of this invention is characterized by the structure of formula II:

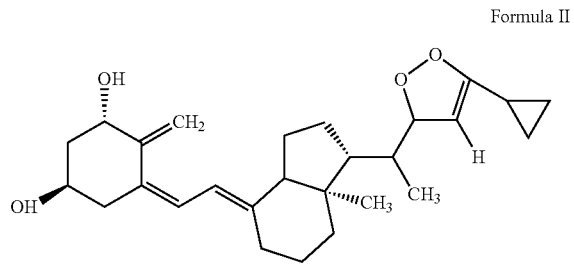

Formula II

In one embodiment, a compound of this invention is characterized by the structure of formula III:

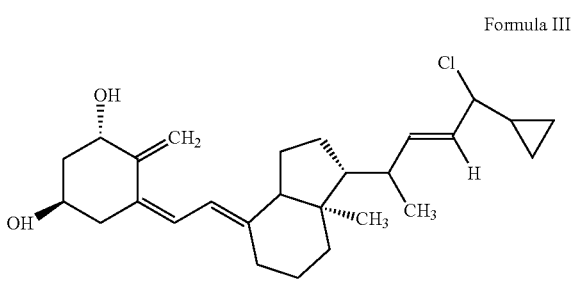

Formula III

In one embodiment, a compound of this invention is characterized by the structure of formula IV:

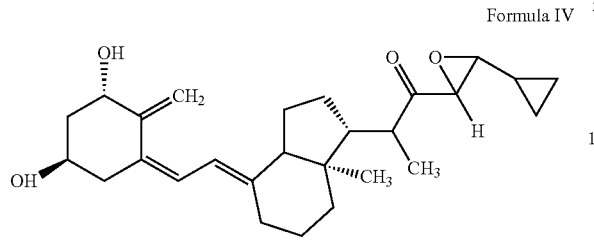

Formula IV

In one embodiment, a compound of this invention is characterized by the structure of formula V:

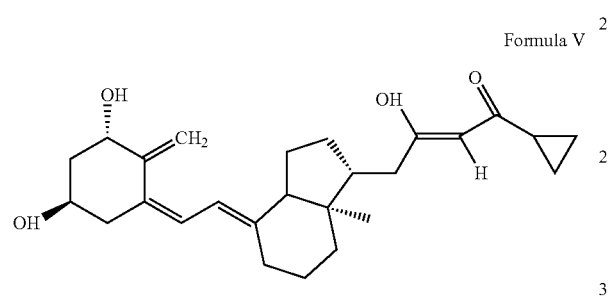

Formula V

In one embodiment, a compound of this invention is characterized by the structure of formula VI:

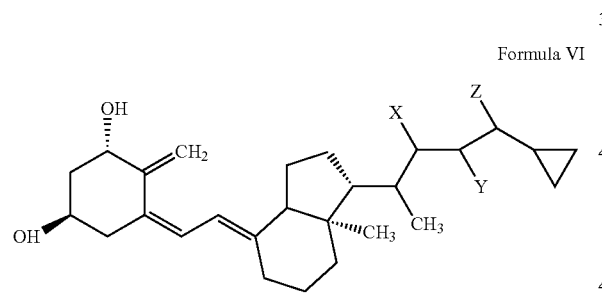

Formula VI wherein X and Y and Z which may be the same or different, are H or OH or oxo groups.

In one embodiment, a compound of this invention is characterized by the structure of formula VII:

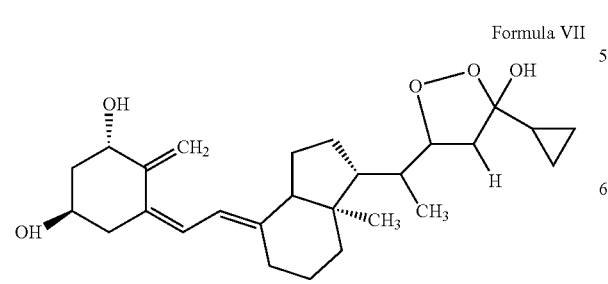

Formula VII

In one embodiment, a compound of this invention is characterized by the structure of formula VIII:

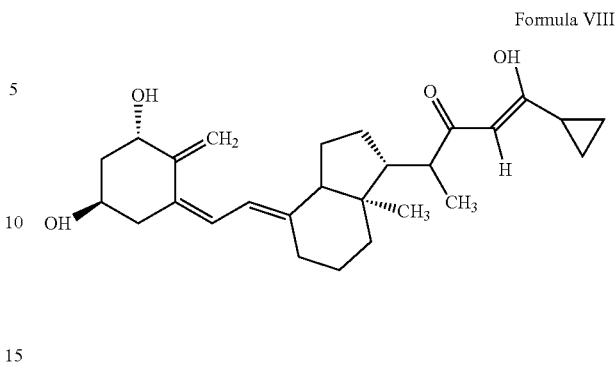

Formula VIII

In one embodiment, a compound of this invention is characterized by the structure of formula IX:

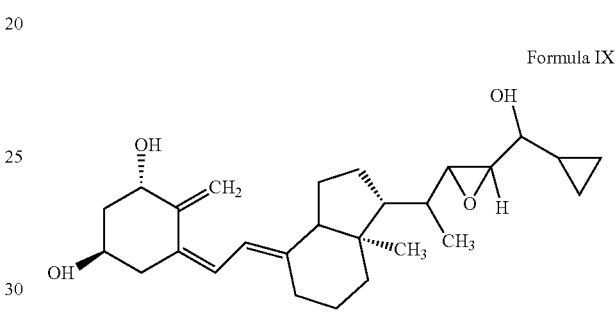

Formula IX

In one embodiment, a compound of this invention is characterized by the structure of formula X:

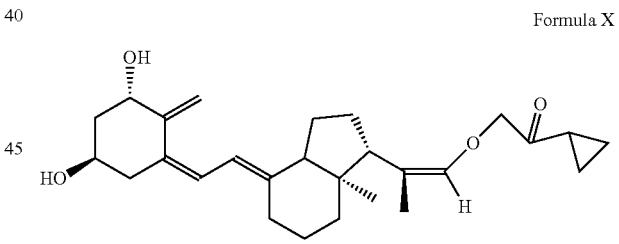

Formula X

In one embodiment, a compound of this invention is characterized by the structure of formula XI:

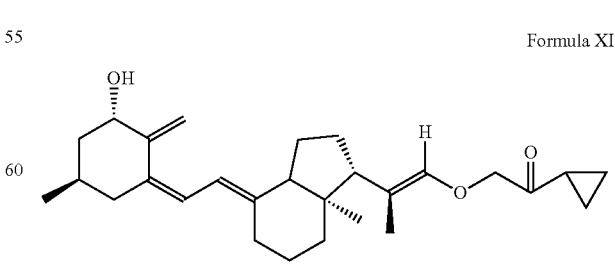

Formula XI

In one embodiment, a compound of this invention is characterized by the structure of formula XII:

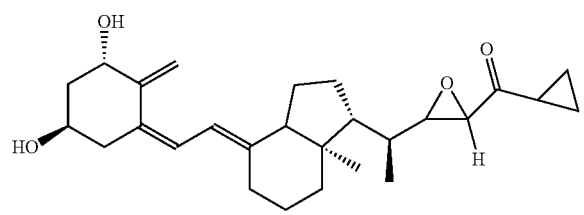

Formula XII

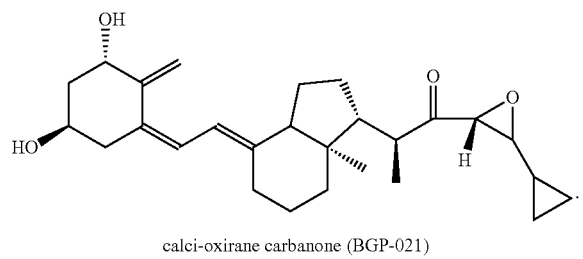

calci-oxirane carbanone (BGP-021)

In one embodiment, a compound of this invention is characterized by the structure of formula XIII:

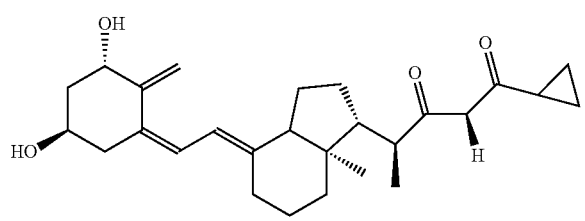

Formula XIII

In one embodiment, a compound of this invention is characterized by the following structure:

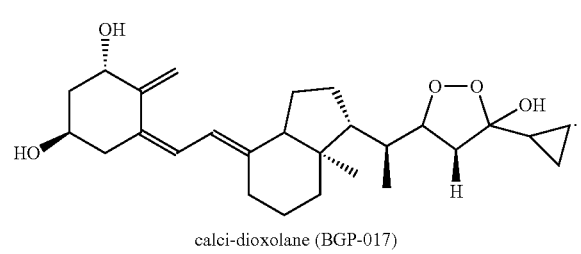

calci-dioxolane (BGP-017)

In one embodiment, a compound of this invention is characterized by the following structure:

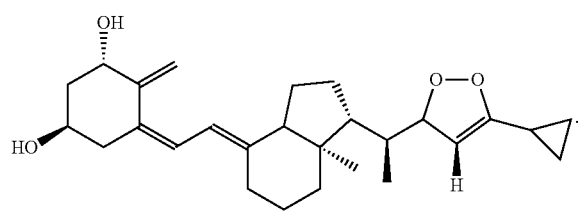

calci-dioxole (BGP-013)

In one embodiment, a compound of this invention is characterized by the following structure:

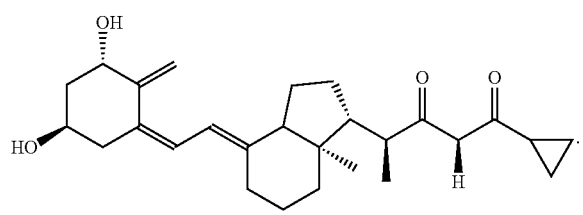

calci-22,24 duone (BGP-019)

In one embodiment, a compound of this invention is characterized by the following structure:

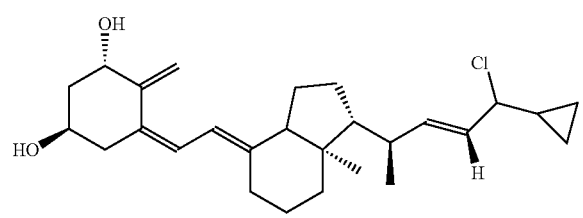

calci-Cl (BGP-015)

In one embodiment, a compound of this invention is characterized by the following structure:

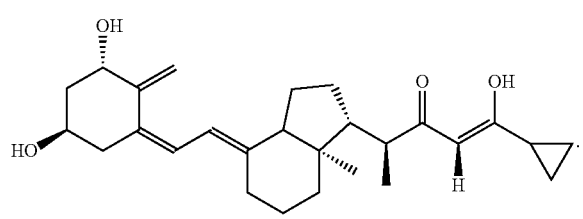

calci-24-OH-22-enal

In one embodiment, a compound of this invention is characterized by the following structure:

In one embodiment, a compound of this invention is characterized by the following structure:

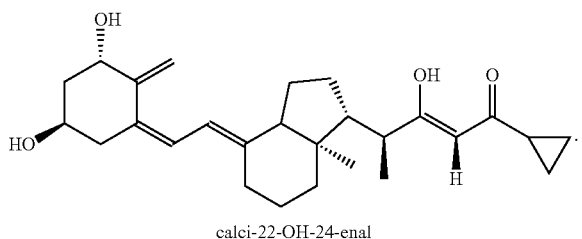

calci-22-OH-24-enal

In one embodiment, this invention provides a composition comprising any compound as described herein. In one embodiment, this invention provides a composition comprising any compound as described herein and a pharmaceutically acceptable excipient.

In one embodiment, this invention provides a composition comprising the compound of formula I.

In one embodiment, the composition comprising the compound of formula I further comprising a pharmaceutically acceptable carrier, diluent, lubricant, flow-aid, or a mixture thereof.

In one embodiment, the composition is in the form of a pellet, a tablet, a capsule, a solution, a suspension, a dispersion, an emulsion, an elixir, a gel, an ointment, a cream, a spray, a dermal patch or a suppository.

In one embodiment, the composition is administered as an oral, intravenous, intraarterial, intramuscular, intracranial, intranasal, subcutaneous, parenteral, transmucosal, transdermal, or topical administration.

In one embodiment, topical administration comprises pasting, spraying, wetting, rubbing, sticking, dispersing, dermal patching the composition or immersing the skin in the composition.

In one embodiment, the composition is a controlled release composition. In one embodiment, the composition is an immediate release composition. In one embodiment, the composition is in a liquid dosage form. In one embodiment, the composition is in a solid dosage form.

In one embodiment, this invention provides a method for treating, reducing incidence, delaying progression or pathogenesis, prolonging remission, inhibiting metastasis, or relieving the symptoms of a cancer in a subject having or predisposed to cancer, said method comprising administering to said subject a compound of formula I.

In one embodiment the cancer is colon, pancreatic, breast or prostate cancer. In one embodiment, the subject has precancerous precursors.

In one embodiment, this invention provides a method for treating, reducing incidence, delaying progression or pathogenesis, or relieving the symptoms of a skin disease or disorder in a subject having or predisposed to having said skin disease or disorder, said method comprising administering to said subject a compound of formula I.

In one embodiment, the skin disease is skin cancer. In one embodiment, the skin cancer is melanoma. In one embodiment, the skin disease is a non-cancerous hyperproliferative skin disease.

In one embodiment, the hyperproliferative skin disease is psoriasis.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 8 shows two graphs: (a) is a graph showing cell internalization kinetics of BGP-13 and CPT as expressed by % entry of the initial quantity applied to cells; and (b) is a graph showing the elimination of BGP-13 and CPT from the external medium with and without 1×10$^7$ cells.

Figure 1A:
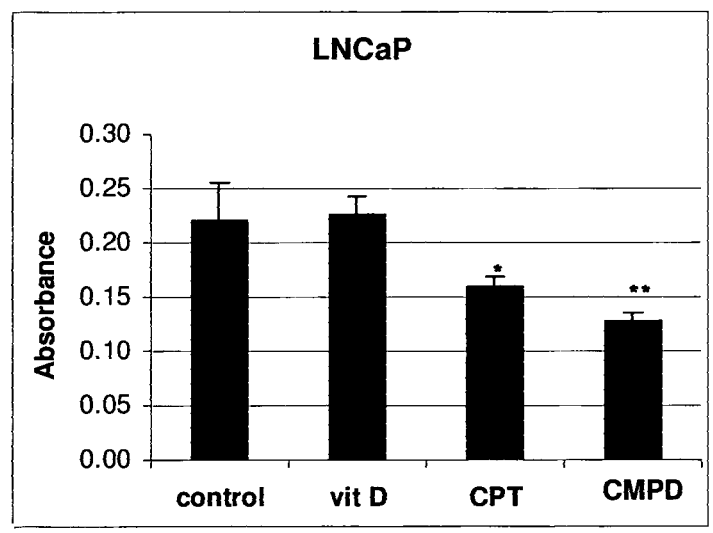
FIG. 1 depicts the results of a viability assay in LNCaP, MCF-7 and HaCaT cell lines following 30 μM treatments with calcitriol (vit D); calcipotriol (CPT) and Compound II for 24 hours. As shown in the figure, Compound II has a much more potent antiproliferative effect on LNCaP and MCF-7 cancer cells than on HaCaT cells. Moreover Compound II has a much more potent antiproliferative effect on LNCaP cells than calcipotriol alone.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, this invention provides compounds and compositions comprising the same, which are useful in treating: hyperparathyroidism, diabetes mellitus, hypertension, acne, alopecia, skin ageing, imbalance in the immune system, inflammatory diseases such as rheumatoid arthritis, asthma, psoriasis and cancer.

In one embodiment the compounds/compositions of this invention are useful in treating dermatological disorders including psoriasis and certain cancer forms, e.g. leukemia and myelofibrosis. The compounds can also inhibit metastasis of these cancers. The compounds are also useful for treatment and prophylaxis of diseases characterized by an imbalance in the immune system, e.g. autoimmune diseases, or AIDS, and to obtain desired immunosuppression as in transplantation procedures, as well as treatment of acne, diabetes mellitus and hypertension and inflammatory diseases, such as rheumatoid arthritis and asthma. As the compounds of this invention may promote the differentiation of the hair follicle cells, these compounds may be used in the treatment of alopecia. In view of the relatively low calcemic effects, these compounds may also be used in the treatment of hyperparathyroidism.

In some embodiments, the compounds/compositions of this invention are useful in treating hyperplasia, such as benign prostatic or cervical hyperplasia. In some embodiments, the compounds/compositions of this invention are useful in treating dysplasia.

In one embodiment this invention provides a compound of formula I:

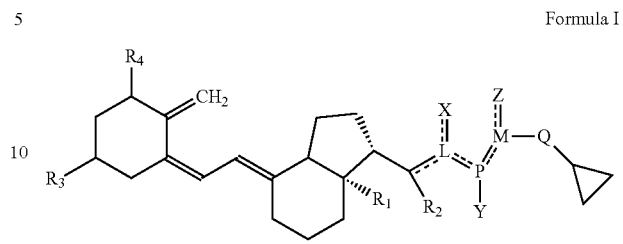

Formula I wherein $R_1$ and $R_2$ are independently H, $C_{(1-4)}$ alkyl, halogen, cycloalkyl;

$R_3$ and $R_4$ are independently OH, OAlk, Alk denoting a $C_{(1-4)}$ alkyl group, halogen, CN, $NH_2$, $NO_2$, $C_{(1-4)}$ alkylene, haloalkyl.

Wherein:

L is carbon and optionally forms a double bond with P or with X, or L forms an epoxide with P;

P is carbon and optionally forms a double bond with L or M, or P forms an epoxide with L or M or P is O;

Q is nothing, or a carbonyl;

M is an alkylene (C1-C4), or optionally a carbon which forms a double bond with P, or M forms an epoxide with P.

Y is nothing, H, OH, OAlk, Alk denoting a $C_{(1-4)}$ alkyl group, O—CO-alkyl.

X is H, oxo, OH, or halogen, OAlk, Alk denoting a $C_{(1-4)}$ alkyl group, O—CO-alkyl.

Z is H, oxo, OH or halogen, OAlk, Alk denoting a $C_{(1-4)}$ alkyl group, O—CO-alkyl.

Or L, P, M, Z and X forms a saturated or unsaturated 5-7 membered, carbocyclic or heterocyclic ring, wherein L, P, M are defined as above and X and Z are independently O, N, S or C.

In one embodiment, a compound of this invention is characterized by the following structure:

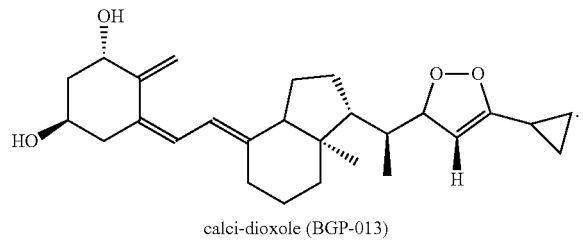

calci-dioxole (BGP-013)

In one embodiment, a compound of this invention is characterized by the following structure:

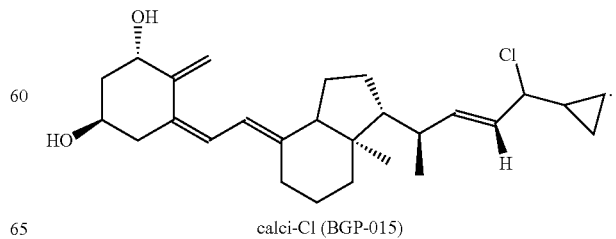

calci-Cl (BGP-015)

In one embodiment, a compound of this invention is characterized by the following structure:

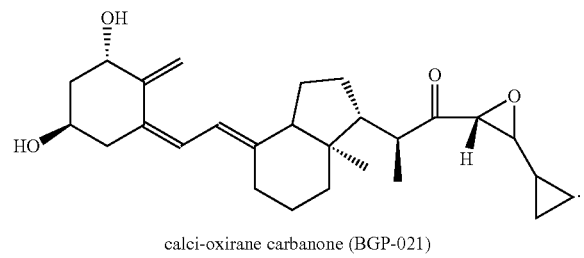
calci-oxirane carbanone (BGP-021)

In one embodiment, a compound of this invention is characterized by the following structure:

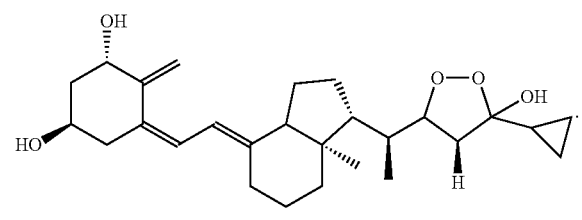
calci-dioxolane (BGP-017)

In one embodiment, a compound of this invention is characterized by the following structure:

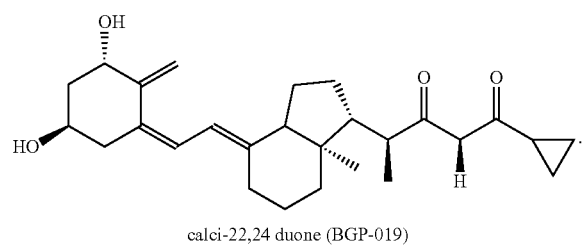
calci-22,24 duone (BGP-019)

In one embodiment, a compound of this invention is characterized by the following structure:

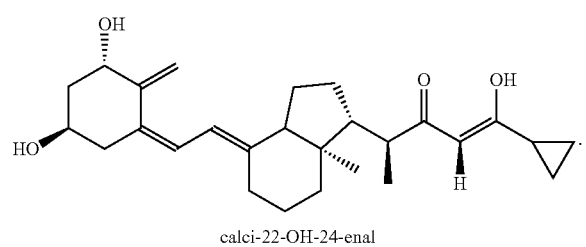
calci-22-OH-24-enal

In one embodiment, a compound of this invention is characterized by the following structure:

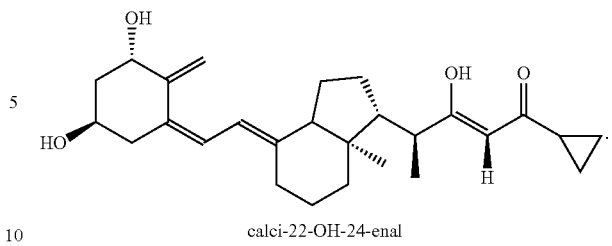
calci-22-OH-24-enal

In one embodiment, this invention provides a compound characterized by the structure of formula II:

Formula II

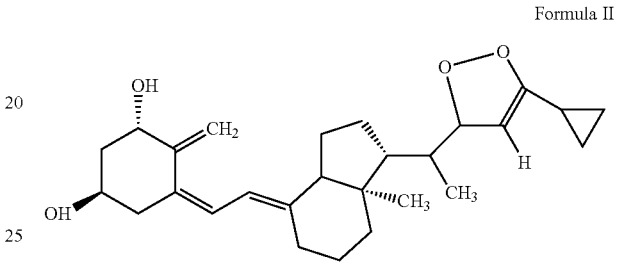

In another embodiment, a compound characterized by the structure of formula II is compound II. In another embodiment, a compound characterized by the structure of formula II is designated as BGP-13.

In one embodiment, this invention provides a compound characterized by the structure of formula III:

Formula III

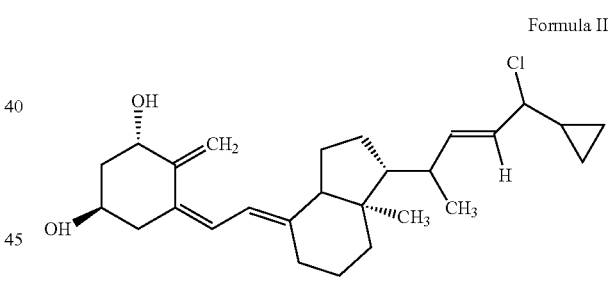

In another embodiment, a compound characterized by the structure of formula III is compound III. In another embodiment, a compound characterized by the structure of formula III is designated as BGP-15.

In one embodiment, this invention provides a compound characterized by the structure of formula IV:

Formula IV

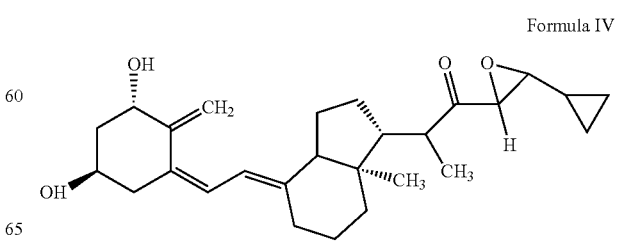

In another embodiment, a compound characterized by the structure of formula IV is compound IV. In another embodiment, a compound characterized by the structure of formula IV is designated as BGP-21.

In one embodiment, this invention provides a compound characterized by the structure of formula V:

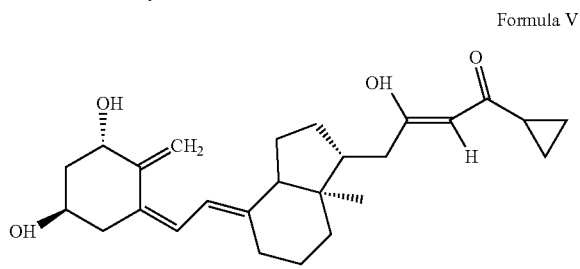

Formula V

In one embodiment, this invention provides a compound characterized by the structure of formula VI:

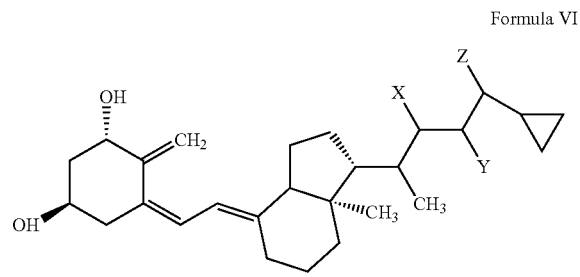

Formula VI wherein X and Y and Z which may be the same or different, are H or OH or oxo groups.

In one embodiment, this invention provides a compound characterized by the structure of formula VII:

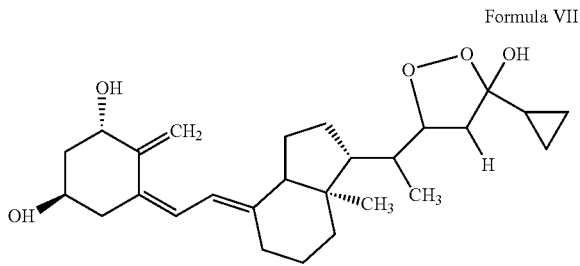

Formula VII

In one embodiment, this invention provides a compound characterized by the structure of formula VIII:

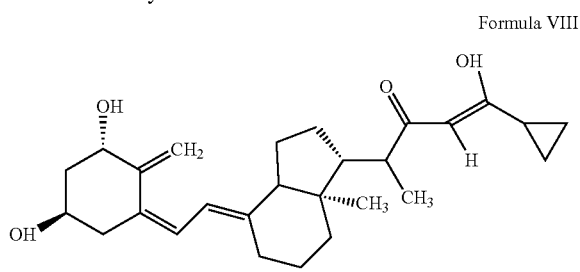

Formula VIII

In one embodiment, this invention provides a compound characterized by the structure of formula IX:

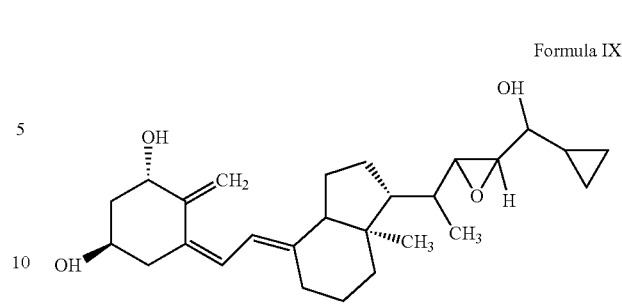

Formula IX

In one embodiment, this invention provides a compound characterized by the structure of formula X:

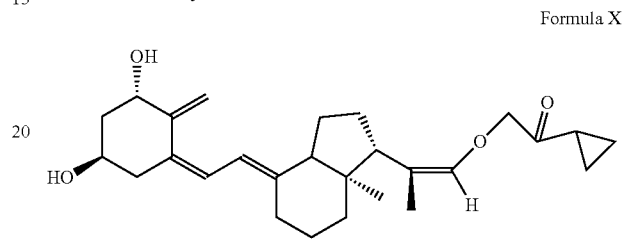

Formula X

In one embodiment, this invention provides a compound characterized by the structure of formula XI:

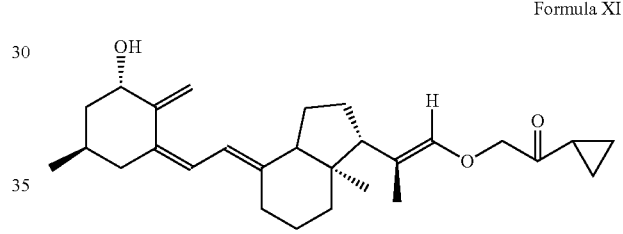

Formula XI

In one embodiment, this invention provides a compound characterized by the structure of formula XII:

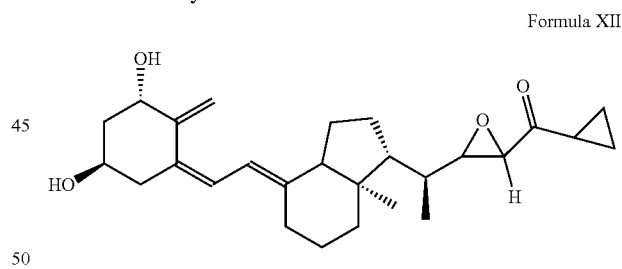

Formula XII

In one embodiment, a compound of this invention is characterized by the structure of formula XIII:

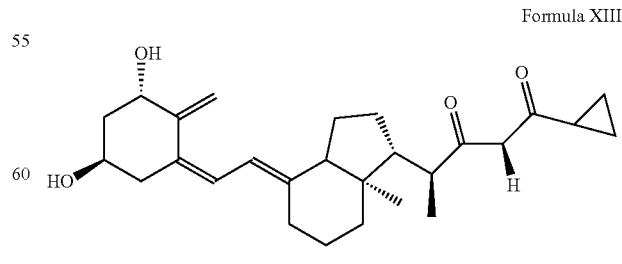

Formula XIII

Chemical Terms

In one embodiment, with reference to the compounds of this invention, the term "alkyl" refers to $C_{1-4}$ straight-chain or $C_{1-4}$ branched hydrocarbons, e.g. methyl, isobutyl, hexyl, etc. In another embodiment, the term "alkyl" (or "lower alkyl") refers to both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amine, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthiols, carbonyls (including ketones, aldehydes, carboxylates, and esters), $-CF_3$, $-CN$ and the like.

In one embodiment, unsaturated 5-7 membered ring refers to aromatic rings such as phenyl, pyridinyl, thienyl, thiazolyl, or furyl, optionally substituted with one or more groups, such as a halo group, a haloalkyl group, an amino group, or an alkyl group. In one embodiment, unsaturated 5-7 membered ring includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $-CF_3$, $-CN$, or the like. Unsaturated 5-7 membered rings also include polycyclic ring systems having two or more rings in which two or more carbons are common to two adjoining rings (the rings are "fused") wherein at least one of the rings is aromatic, e.g., the other rings can be cycloalkyls, cycloalkenyls, cycloalkynyls, aryls and/or heterocyclyls.

In one embodiment, the term $NH_2$ group or "amine" refers to any amine, including primary, secondary, tertiary, or a quaternary ammonium salts, or a combination thereof, as applicable herein.

In one embodiment, a nitro group is synonymous with $NO_2$ and refers to any nitro group as applicable herein. In one embodiment, a cyano group is synonymous with CN and refers to any cyano group as applicable herein. A cyano or cyanide is any chemical compound that contains the cyano group (C≡N), which consists of a carbon atom triple-bonded to a nitrogen atom. In one embodiment, cyanide specifically is the anion $CN^-$. The compounds containing the cyanide as a functional group are also referred to as nitriles.

In one embodiment, the term alkylene is synonymous with the term alkene. In one embodiment, the term alkene refers to an olefin. In one embodiment, alkylene is an unsaturated chemical compound or functional group containing at least one carbon-to carbon double bond. In one embodiment, simple acyclic alkenes, with only one double bond and no other functional group form a homologous series of hydrocarbons with the general formula $C_nH_{2n}$. In one embodiment, members of this homologous series are included as alkylene groups of this invention.

In one embodiment, haloalkyl refers to an alkyl substituted with a halogen. In one embodiment, halogen refers to the nonmetal elements from group 17 of the periodic table. In one embodiment halogen comprising fluorine, F; chlorine, Cl; bromine, Br; iodine, I; and astatine, At. In one embodiment, haloalkyls of this invention may be haloalkyls, dihaloalkyls, trihaloalkyls, or tetra haloalkyls. In one embodiment any number of halogen atoms can substitute an alkyl chain or group in compounds of this invention.

In one embodiment, "heterocyclic" refers to ring structures containing atoms in addition to carbon, such as sulfur, oxygen or nitrogen, as part of the ring. They may be either simple aromatic rings or non-aromatic rings. Some examples are pyridine $(C_5H_5N)$, pyrimidine, $(C_4H_4N_2)$ and dioxane $(C_4H_8O_2)$. In one embodiment, "carbocyclic" refers to a ring structure containing carbon atoms only. They may be either aromatic rings or non-aromatic rings.

In another embodiment, this invention provides compositions comprising a compound of this invention, as described herein, or, in another embodiment, a combination of an analog, derivative, isomer, metabolite, pharmaceutically acceptable salt, pharmaceutical product, hydrate, N-oxide, prodrug, polymorph, impurity or crystal of the compounds of the present invention.

In one embodiment, the term "isomer" includes, but is not limited to, optical isomers and analogs, structural isomers and analogs, conformational isomers and analogs, and the like.

In one embodiment, the term "isomer" is meant to encompass optical isomers of the polymer. It will be appreciated by those skilled in the art that the polymer of the present invention contain at least one chiral center. Accordingly, the polymer used in the methods of the present invention may exist in, and be isolated in, optically-active or racemic forms. Some compounds may also exhibit polymorphism. It is to be understood that the present invention encompasses any racemic, optically-active, polymorphic, or stereoisomeric form, or mixtures thereof, which form possesses properties useful in the treatment of androgen-related conditions described herein. In one embodiment, the polymer are the pure (R)-isomers. In another embodiment, the polymers are the pure (S)-isomers. In another embodiment, the polymers are a mixture of the (R) and the (S) isomers. In another embodiment, the polymers are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes "pharmaceutically acceptable salts" of the compound of this invention, which may be produced, in one embodiment, using an amino-substituted compound and an organic and inorganic acids, for example, citric acid and hydrochloric acid. Pharmaceutically acceptable salts can be prepared, from the phenolic compounds, in other embodiments, by treatment with inorganic bases, for example, sodium hydroxide. In another embodiment, esters of the phenolic compounds can be made with aliphatic and aromatic carboxylic acids, for example, acetic acid and benzoic acid esters. As used herein, "pharmaceutically acceptable salt" refers to, in one embodiment, those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in J. Pharmaceutical Sciences, 1977, 66: 1-19. The salts can be prepared in situ during the final isolation and purification of the compounds of the invention, or separately by reacting the free base function with a suitable organic acid. Representative acid addition salts include acetate, adipate, alginate, ascorbate, aspartate, benzene-sulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary as ammonium, and mine cations, including, but not limited to ammonium, tetramethylammonium, tetraethylammonium, methylamine, dimethylamine, trimethylamine, triethylamine, ethylamine, and the like.

The invention also includes N-oxides of the amino substituents of the compound described herein.

This invention provides derivatives of the compounds. In one embodiment, "derivatives" includes but is not limited to ether derivatives, acid derivatives, amide derivatives, ester derivatives and the like. In another embodiment, this invention further includes hydrates of the compounds. In one embodiment, hydrate is a term used to indicate that a substance contains water or water molecules. In one embodiment, "hydrate" includes but is not limited to hemihydrate, monohydrate, dihydrate, trihydrate and the like.

This invention provides, in other embodiments, metabolites of the compounds. In one embodiment, "metabolite" means any substance produced from another substance by metabolism or a metabolic process.

This invention provides, in other embodiments, pharmaceutical products of the compounds of this invention. The term "pharmaceutical product" refers, in other embodiments, to a composition suitable for pharmaceutical use (pharmaceutical composition), for example, as described herein.

Compositions

In one embodiment this invention provides a pharmaceutical composition comprising to the compounds of this invention.

In one embodiment the composition further comprises a carrier, diluent, lubricant, flow-aid, or a mixture thereof. In one embodiment the composition is in the form of a pellet, a tablet, a capsule, a solution, a suspension, a dispersion, an emulsion, an elixir, a gel, an ointment, a cream, an I.V. solution, a spray, a dermal patch or a suppository. In one embodiment the composition is in the form of a capsule. In one embodiment the composition is in a form suitable for oral, intravenous, intraarterial, intramuscular, intracranial, intranasal, subcutaneous, parenteral, transmucosal, transdermal, intratumoral or topical administration. In one embodiment the composition is a controlled release composition. In one embodiment the composition is an immediate release composition. In one embodiment the composition is a liquid dosage form. In one embodiment the composition is a solid dosage form. In one embodiment the composition further comprises an additional antineoplastic compound, an immunotherapeutic agent or an additional drug.

In another embodiment, this invention provides a composition comprising a compound of this invention. In one embodiment this invention provides a pharmaceutical composition comprising the compounds of the present invention.

In one embodiment the composition further comprising a carrier, diluent, lubricant, flow-aid, or a mixture thereof. In one embodiment the composition is in the form of a pellet, a tablet, a capsule, a solution, a suspension, a dispersion, an emulsion, an elixir, a gel, an ointment, a cream, an I.V. solution or a suppository. In one embodiment the composition is in the form of a capsule.

Pharmaceutical compositions of this invention for parenteral injection comprise pharmaceutically acceptable sterile aqueous or nonaqueous solutions, dispersions, suspensions, or emulsions as well as sterile powders for reconstitution into sterile injectable solutions or dispersions just prior to use. Examples of suitable aqueous and nonaqueous carriers, diluents, solvents, or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

In one embodiment the composition is in a form suitable for oral, intravenous, intraarterial, intramuscular, intracranial, intranasal, subcutaneous, parenteral, transmucosal, transdermal, rectally, intracisternally, intravaginally, intraperitoneally, topically (as by powders, ointments, dermal patches, sprays or drops), bucally, or as an oral or nasal spray. The term "parenteral" administration as used herein refers to modes of administration which include intravenous, intramuscular, intraperitoneal, intrathecally, intrasternal, subcutaneous and intraarticular injection and infusion.

In one embodiment the composition can be administered to humans and other animals. In one embodiment the composition is a controlled release composition. In one embodiment the composition is an immediate release composition. In one embodiment the composition is a liquid dosage form. In one embodiment the composition is a solid dosage form. In one embodiment the composition further comprising an antineoplastic compound, an immunotherapeutic agent or a drug. In one embodiment, the compositions of this invention, which comprise a polymer of this invention is biocompatible, and in another embodiment, may comprise pharmaceutically acceptable carriers or excipients, such as disclosed in Remington's Pharmaceutical Sciences, Mack Publishing Company, Easton, Pa., USA, 1985. These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the compounds as drugs, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Compositions for rectal or vaginal administration are, in one embodiment, suppositories which can be prepared by mixing the compounds of this invention with suitable non-irritating excipients or carriers such as cocoa butter, polyethylene glycol, or a suppository wax which are solid at room temperature but liquid at body temperature and therefore melt in the rectum or vaginal cavity and release the active compound.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the polymer compound of the present invention, stabilizers, preservatives, excipients, and the like. In one embodiment, the lipids may be natural or synthetic phospholipids or a combination thereof.

Methods to form liposomes are known in the art. See, for example, Prescott, Ed., Methods in Cell Biology, Volume XIV, Academic Press, New York, N.Y. (1976), p. 33 et seq.

The compounds of the present invention can also be administered as dendrimers, as functional groups on a dendrimer or trapped inside a dendrimer. As known in the art, dendrimers are repeatedly branched molecules. Their core structure is a molecule with at least two, and preferably more identical functional groups. The functional groups on this core molecule serve as an anchor for molecules bearing typically at least three of the same or similar functional groups. A layer of molecules can be bound to the first core molecule thus forming the first generation of the dendrimer. Since these molecules possess the same functional groups as the core molecules, they can bind an additional layer of molecules forming the second generation of the dendrimer. This scheme is then repeated until the desired number of generations is achieved. This repetition forms a branched structure in which each generation contains more molecules than the previous one. The branched nature of the dendrimer is the result of the branching ability of each molecule. The branching ability is reflected by the multiple functional groups of each molecule. Similar to a tree (which is the origin of the name), the number of branches grows from generation to generation. Compounds encapsulated in dendrimers can be slow-released into the environment, thus providing an advantage for various therapies.

In one embodiment compounds of the present invention can be mixed with a polymer and can be administered with a polymer or a polymeric particle. Similar to dendritic structures described herein above, polymers or polymeric particles can provide controlled release of the drug or the compound trapped in it.

Compounds of this invention can be bound to microparticles or nanoparticles and administered in this form. The micro/nano particles can be organic or inorganic. The compounds can become in contact with the desired tissue or area, they can be released from the particle by a cleaving agent or by the interaction of radiation with the particles. One aspect of radiation-induced release is a drug release that is induced by particle heating. Particles may further comprise a marker which can help in detecting the spatial location of the drug. Markers can help the controlled activation of the drug by assessing the location of the particle, and inducing release of the drug accordingly.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved.

The pharmaceutical compositions of the present invention can be used in both veterinary medicine and human therapy. The magnitude of a prophylactic or therapeutic dose of the pharmaceutical composition of the invention will vary with the severity of the condition to be treated and the route of administration. The dose, and perhaps the dose frequency, will also vary according to the age, body weight, and response of the individual patient.

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

In one embodiment, the compounds or compositions of this invention are used as a drug. In one embodiment, the term "drug" refers to a substance applicable for use in the diagnosis, or in another embodiment, cure, or in another embodiment, mitigation, or in another embodiment, treatment, or in another embodiment, prevention of a disease, disorder, condition or infection. In one embodiment, the term "drug" refers to any substance which affects the structure or function of the target to which it is applied.

In another embodiment, the term "drug" refers to a molecule that alleviates a symptom of a disease or disorder when administered to a subject afflicted thereof.

In one embodiment, compounds or compositions of this invention may comprise an agent, which is useful in halting or altering the course of frank neoplasia or metastasis. In some embodiments, the compound is cytotoxic to neoplastic cells or preneoplastic cells selectively, or in some embodiments, preferentially. In some embodiments, two or more compounds may be incorporated in compositions of the invention, where the first drug is cytotoxic to the neoplastic or preneoplastic cells, and the second, etc. drug is protective of healthy tissue.

In another embodiment, compositions of this invention may further comprise other antineoplastic agents such as platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, paclitaxel and other taxenes, rapamycin, manumycin A, TNP-470, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, interferon .alpha.-2a, interferon .alpha.-2b, teniposide (VM-26), vinblastine sulfate (VLB), vincristine sulfate, bleomycin sulfate, hydroxyurea, procarbazine, and dacarbazine; mitotic inhibitors such as etoposide, colchicine, and the vinca alkaloids, radiopharmaceuticals such as radioactive iodine and phosphorus products; hormones such as progestins, estrogens and antiestrogens; anti-helmintics, antimalarials, and antituberculosis drugs; biologicals such as immune serums, antitoxins and antivenoms; rabies prophylaxis products; bacterial vaccines; viral vaccines; biological response modifiers such as muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-alanyl-D-isoglutamine; anti-fungal agents such as ketoconazole, nystatin, griseofulvin, flucytosine (5-fc), miconazole, amphotericin B, ricin, cyclosporins, and β-lactam antibiotics (e.g., sulfazecin); hormones such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, vassopressin, and their derivatives; vitamins such as cyanocobalamin neinoic acid, retinoids and derivatives such as retinol palmitate, and .alpha.-tocopherol; peptides, such as manganese super oxide dismutase; enzymes such as alkaline phosphatase; anti-allergic agents such as amelexanox; antituberculars such as para-aminosalicylic acid, isoniazid, capreomycin sulfate cycloserine, ethambutol hydrochloride ethionamide, pyrazinamide, rifampin, and streptomycin sulfate; antivirals such as amantadine azidothymidine (AZT, DDI, Foscarnet, or Zidovudine), ribavirin and vidarabine monohydrate (adenine arabinoside, ara-A); antianginals such as diltiazem, nifedipine, verapamil, erythritol tetranitrate, isosorbide dinitrate, nitroglycerin (glyceryl trinitrate) and pentaerythritol tetranitrate; antiinflammatories such as diflunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; radioactive particles or ions such as strontium, iodide rhenium and yttrium, or any combination of drug or agent as herein described.

In another embodiment, compounds of this invention has a therapeutic effect. In one embodiment, the term "therapeutic", refers to a molecule, which when provided to a subject in need, provides a beneficial effect.

In another embodiment, compositions of this invention may further comprise a growth factor, or a tissue-promoting factor.

In one embodiment the compounds or compositions or drugs of this invention may comprise a toxin. In one embodiment, the term "toxin" refers to a molecule which results in toxic effects in cells and/or tissue exposed to the toxin. In one embodiment, the toxin results in cell death, or in another embodiment, cell damage. In one embodiment, the toxin results in an increase in cell size. In one embodiment, the increased cell size induced by the toxin is an indication of a non-apoptotic death pathway.

In one embodiment, the effective amounts of compounds of this invention given to a subject is tailored to the subject needs and to the condition treated. In one embodiment, compounds are given in an administration protocol in a variety of dose ranges depending on the particular need of the patient. One such suitable dose range is from 0.01 µg to 400 µg. Another suitable dose range is administered on a daily basis per kilogram of body weight, the dose ranges being from 0.001 µg/kg/day to 5.0 µg/kg/day. Another dosing regimen calls for a high dosage, generally 10 µg/dose or greater up to 400 µg/dose or greater, given episodically or intermittently. The protocol or dosage regimen in accordance with the present invention provides an improved therapeutic index. In an episodic dosing, a lower quantity of active agent might be needed.

In one embodiment, compositions of the present invention can be formulated for treating a subject according to personalized medicine. In one embodiment, personalized medicine describes the use of information and data from a patient's genotype, or level of gene expression to stratify disease, select a medication, provide a therapy, or initiate a preventative measure that is particularly suited to that patient at the time of administration. In addition to genetic information, other factors, including imaging, laboratory, and clinical information about the disease process or the patient play an equally important role. Personalized medicine is directed toward the possibility to give the appropriate drug, at the appropriate dose, to the appropriate patient, at the appropriate time. The benefits of this approach are in its accuracy, efficacy, safety and speed. Personalized medicine is a new approach to drug development with the potential of effective diagnosis, therapeutics, and patient care. Personalized medicine develops patient-specific tests that monitor the effectiveness of treatment and that can identify the recurrence of a disease in an early stage.

In some embodiments this invention is related to the treatment of cancer or other conditions in a subject by administering compounds and/or compositions of the present invention. In one embodiment this invention provides a method of treating an inflammatory condition in a subject, the method comprising administering a compound of the present invention to a subject.

In one embodiment this invention provides a method of treating, reducing the incidence of, delaying progression of, reducing the pathogenesis of, prolonging remission of cancer or inhibiting metastasis of a cancer in a subject, the method comprising the step of contacting a neoplastic cell in a subject with a compound of the present invention.

In one embodiment the method of treating, reducing the incidence of, delaying progression of, reducing the pathogenesis of, prolonging remission of cancer or inhibiting metastasis of a cancer in a subject, further comprising the step of providing adjunct anti cancer therapy to said subject. In one embodiment the adjunct anti-cancer therapy comprises surgery, chemotherapy, radiation or a combination thereof.

In one embodiment, the term "treating" refers to curing a disease. In another embodiment, "treating" refers to preventing a disease. In another embodiment, "treating" refers to reducing the incidence of a disease. In another embodiment, "treating" refers to inducing remission. In another embodiment, "treating" refers to slowing the progression of a disease. The terms "reducing", "suppressing" and "inhibiting" refer in one embodiment, to lessening or decreasing. The term "progression" may refer to increasing in scope or severity, advancing, growing or becoming worse. The term "recurrence" refers, in one embodiment, to the return of a disease after a remission.

In one embodiment, the term "administering" refers to bringing a subject in contact with a nucleotide molecule of the present invention. In another embodiment, administration is accomplished in vitro, i.e. in a test tube. In another embodiment, administration is accomplished in vivo, i.e. in cells or tissues of a living organism. Each possibility represents a separate embodiment of the present invention.

In one embodiment cancers are classified by the type of cell that resembles the tumor and, therefore, the tissue presumed to be the origin of the tumor. In one embodiment the cancer type is carcinoma, in which Malignant tumors are derived from epithelial cells. In one embodiment carcinoma represents the most common cancers, including the common forms of breast, prostate, lung and colon cancer. In another embodiment the cancer type is sarcoma. In one embodiment this type of cancer comprises malignant tumors derived from connective tissue, or mesenchymal cells. In another embodiment the cancer type is lymphoma or leukemia. In one embodiment this cancer type comprises malignancies derived from hematopoietic (blood-forming) cells. In another embodiment the cancer type is in the form of a germ cell tumor. In one embodiment such tumor is derived from totipotent cells. In another embodiment, the tumor is a blastic tumor. In one embodiment this is a usually malignant tumor which resembles an immature or embryonic tissue.

In some embodiments, the compounds/compositions and methods of this invention are useful in treating any tumor, for example, a solid tumor, including but not limited to, carcinomas of the lung, breast, ovary, stomach, pancreas, larynx, esophagus, testes, liver, parotid, bilary tract, colon, rectum, cervix, uterus, endometrium, kidney, bladder, prostrate, thyroid, squamous cell carcinomas, adenocarcinomas, small cell carcinomas, melanomas, gliomas, neuroblastomas, sarcomas (e.g., angiosarcomas, chondrosarcomas).

In some embodiments, the compounds/compositions and/or methods of this invention comprise treating a cancer wherein the subject is provided other anti-cancer adjunct therapy, for example, including radiation, chemotherapy and surgical removal of neoplastic cells or tissue. In some embodiments, such adjunct therapy may comprise administration of other chemotherapeutic agents (e.g., alkylating agents (e.g., nitrogen mustards (e.g., cyclophosphamide, ifosfamide, mechlorethamine, melphalen, chlorambucil, hexamethylmelamine, thiotepa), alkyl sulfonates (e.g., busulfan), nitrosoureas, triazines) antimetabolites (e.g., folic acid analogs, pyrimidine analogs (e.g., fluorouracil, floxuridine, cytosine arabinoside, etc.), purine analogs (e.g., mercaptopurine, thiogunaine, pentostatin, etc.), natural products (e.g., vinblastine, vincristine, etoposide, tertiposide, dactinomycin, daunorubicin, doxurubicin, bleomycin, mithrmycin, mitomycin C, L-asparaginase, interferon alpha), platinum coordination complexes (e.g., cis-platinum, carboplatin, etc.), mitoxantrone, hydroxyurea, procarbazine, hormones and antagonists (e.g., prednisone, hydroxyprogesterone caproate, medroxyprogesterone acetate, megestrol acetate, diethylstilbestrol, ethinyl estradiol, tamoxifen, testosterone propionate, fluoxymesterone, flutamide, leuprolide, etc.), other anti-angiogenesis agents or inhibitors (e.g., angiostatin, retinoic acids and paclitaxel, estradiol derivatives, thiazolopyrimidine derivatives, etc.), apoptosis-inducing agents (e.g., antisense nucleotides that block oncogenes which inhibit apoptosis, tumor suppressors, TRAIL, TRAIL polypeptide, Fas-associated factor 1, interleukin-1β-converting enzyme, phosphotyrosine inhibitors, RXR retinoid receptor agonists, carbostyril derivatives, etc.) or chelators (penicillamine, zinc, trientine, etc.). In some embodiments, such compounds may be conjugated to the compounds of the invention, and/or be supplied in trans, as part of a second composition.

In one embodiment, compounds and compositions of this invention are useful in treating cancer by inhibiting proliferation. In one embodiment, compounds and compositions of this invention are useful in treating cancer by inducing or stimulation of cell differentiation. In one embodiment, compounds and compositions of this invention are useful in treating cancer by causing cell death. In one embodiment, cell death is apoptotic. In one embodiment cell death is not apoptotic. In one embodiment, cell size is increased. In one embodiment, the mechanism of tumor growth inhibition is associated with cell size increase. In some embodiments, compounds of the invention possess antileukemic activity by virtue of inducing the differentiation of malignant cells (specifically leukemia cells) to nonmalignant macrophages (monocytes), and are useful in the treatment of leukemia. In one embodiment, Antiproliferative and differentiating actions of the compounds on cancer cell lines is shown. In one embodiment, compounds of the invention bind to vitamin D receptor thus reducing cancer risk. In one embodiment, vitamin D receptors have a role in the development, and possible treatment, of cancer, and vitamin D analogs of this invention affect the vitamin D receptors to promote cancer treatment or reduce forms of cancer, tumors and undesired proliferation processes.

In one embodiment, compounds of this invention, unlike existing vitamin D analogs, are highly effective in promoting differentiation in malignant cells, and their practical use in differentiation therapy as anticancer agents is enabled because of their low affect on calcium metabolism. In one embodiment, compounds of the invention do not elevate blood calcium to an undesired level through their calcemic activity. In one embodiment, compounds of this invention do not lead to hypercalcemia. In one embodiment, compounds of this invention possess lower calcemic activity than other existing vitamin D analogs.

In other embodiments, the compounds of this invention are useful in treating any disease associated with undesirable cell proliferation. The compositions and methods of the present invention can also treat chronic inflammatory conditions, for example psoriasis or diseases associated with psoriasis. Psoriasis, a skin disease, is another chronic and recurrent disease that is characterized by papules and plaques of various sizes. In some embodiments, the compounds/compositions and methods are useful in treating inflammation.

In one embodiment, compounds and compositions of this invention are useful in treating subjects suffering from psoriasis. Psoriasis is a disease which affects the skin and the joints. It commonly causes red scaly patches to appear on the skin. The scaly patches caused by psoriasis, called psoriatic plaques, are areas of inflammation and excessive skin production. Skin rapidly accumulates at these sites and takes a silvery-white appearance. Plaques frequently occur on the skin of the elbows and knees, but can affect any area including the scalp and the genitals. Psoriasis is hypothesized to be an immune-mediated disease and it is not contagious.

The disorder is a chronic recurring condition which varies in severity from minor localized patches to complete body coverage. Fingernails and toenails are frequently affected (psoriatic nail dystrophy) and can be seen as an isolated finding. Psoriasis can also cause inflammation of the joints, which is known as psoriatic arthritis. Ten to fifteen percent of people with psoriasis have psoriatic arthritis.

The cause of psoriasis is not known, but it is believed to have a genetic component. Several factors are thought to aggravate psoriasis. These include stress, excessive alcohol consumption and smoking. Individuals with psoriasis may suffer from depression and loss of self-esteem. As such, quality of life is an important factor in evaluating the severity of the disease. There are many treatments available but because of its chronic recurrent nature psoriasis is a challenge to treat.

In some embodiment, compounds and compositions of this invention are useful in the treatment of plaque, flexural, guttate, pustular or nail psoriasis.

Plaque psoriasis (psoriasis vulgaris) is the most common form of psoriasis. It affects 80 to 90% of people with psoriasis. Plaque psoriasis typically appears as raised areas of inflamed skin covered with silvery white scaly skin. These areas are called plaques. Flexural psoriasis (inverse psoriasis) appears as smooth inflamed patches of skin. It occurs in skin folds, particularly around the genitals (between the thigh and groin), the armpits, under an overweight stomach, and under the breasts (inframammary fold). It is aggravated by friction and sweat, and is vulnerable to fungal infections.

Guttate psoriasis is characterized by numerous small oval (teardrop-shaped) spots. These numerous spots of psoriasis appear over large areas of the body, such as the trunk, limbs, and scalp. Guttate psoriasis is associated with streptococcal throat infection.

Pustular psoriasis appears as raised bumps that are filled with non-infectious pus (pustules). The skin under and surrounding pustules is red and tender. Pustular psoriasis can be localized, commonly to the hands and feet (palmoplantar pustulosis), or generalized with widespread patches occurring randomly on any part of the body.

Nail psoriasis produces a variety of changes in the appearance of finger and toe nails. These changes include discoloring under the nail plate, pitting of the nails, lines going across the nails, thickening of the skin under the nail, and the loosening (onycholysis) and crumbling of the nail.

In some embodiment, compounds and compositions of this invention are useful in the treatment of psoriatic arthritis. Psoriatic arthritis involves joint and connective tissue inflammation. Psoriatic arthritis can affect any joint but is most common in the joints of the fingers and toes. This can result in a sausage-shaped swelling of the fingers and toes known as dactylitis. Psoriatic arthritis can also affect the hips, knees and spine spondylitis. About 10-15% of people who have psoriasis also have psoriatic arthritis.

In some embodiment, compounds and compositions of this invention are useful in the treatment of Erythrodermic psoriasis. Erythrodermic psoriasis involves the widespread inflammation and exfoliation of the skin over most of the body surface. It may be accompanied by severe itching, swelling and pain. It is often the result of an exacerbation of unstable plaque psoriasis, particularly following the abrupt withdrawal of systemic treatment. This form of psoriasis can be fatal, as the extreme inflammation and exfoliation disrupt the body's ability to regulate temperature and for the skin to perform barrier functions.

In some embodiment, compounds and compositions of this invention are useful in the treatment of mild, moderate or severe psoriasis. Psoriasis is usually graded as mild if affecting less than 3% of the body. Psoriasis is usually graded moderate if affecting 3-10% of the body. Psoriasis is usually graded as severe if affecting more than 10% of the body. Several scales exist for measuring the severity of psoriasis. The degree of severity is generally based on the following factors: the proportion of body surface area affected; disease activity (degree of plaque redness, thickness and scaling); response to previous therapies; and the impact of the disease on the person.

The psoriasis area severity index (PASI) is the most widely used measurement tool for psoriasis. PASI combines the assessment of the severity of lesions and the area affected into a single score in the range 0 (no disease) to 72 (maximal disease). Nevertheless, the PASI can be too unwieldy to use outside of trials, which has led to attempts to simplify the index for clinical use.

In some embodiment, compounds and compositions of this invention are useful in the treatment of psoriasis with low or no adverse reactions. In some embodiments the compounds and compositions have low or high or moderate toxicity. In some embodiments treatment of psoriasis with compounds or compositions of this invention is conducted in parallel to phototherapy. In one embodiment, in phototherapy the skin is exposed to ultraviolet (UV) radiation. Phototherapy may involve the use of medications which are taken internally by pill or injection. This approach is called systemic treatment. Compounds and compositions of this invention may be part of a systemic treatment, of a photochemotherapy treatment, or as a supplement to any of the treatments mentioned herein above.

In some embodiment, compounds and compositions of this invention are useful in the treatment of psoriasis that has become resistant to a specific therapy. Treatments and doses involving compounds and compositions of this invention may be periodically changed to prevent resistance developing (tachyphylaxis) and to reduce the chance of adverse reactions occurring. In some embodiments this is called treatment rotation.

In some embodiment, compounds and compositions of this invention are useful in the treatment of psoriasis by their utilization in bath solutions and moisturizers that help soothe affected skin and reduce the dryness which accompanies the build-up of skin on psoriatic plaques. In one embodiment, medicated creams and ointments comprising compounds of this invention, applied directly to psoriatic plaques can help reduce inflammation, remove built-up scale, reduce skin turn over, and clear affected skin of plaques. In one embodiment, ointment and creams comprising compounds of this invention and further containing coal tar, dithranol (anthralin), corticosteroids like topicort, and retinoids are used. In some embodiments Argan oil is used in conjunction with compounds of this invention for special treatments. In some embodiment, treating psoriasis with compounds of this invention helps to normalize skin cell production and reduce inflammation. In some embodiment, treating psoriasis with compounds of this invent is highly effective as the compounds function as inhibitors of skin cell proliferation.

In some embodiments, compounds of this invention are used to treat recurrence of psoriasis after other systemic treatment was discontinued.

In one embodiment, compounds of this invention are used to treat psoriasis before, after or in conjunction with the three main traditional systemic psoriasis treatments. The three traditional systemic treatments are with methotrexate, cyclosporine and retinoids. Methotrexate and cyclosporine are immunosupressant drugs and retinoids are synthetic forms of vitamin A. Other additional drugs include the antimetabolite tioguanine, the cytotoxic agent hydroxyurea, sulfasalazine, the immunosupressants mycophenolate mofetil, azathioprine and oral tacrolimus. These have all been used to treat psoriasis and are used with compounds of this invention in one embodiment. In addition to compounds of this invention, fumaric acid esters are used to treat severe psoriasis in one embodiment.

In one embodiment, biologics are used with compounds of this invention for the treatment of psoriasis. Biologics are manufactured proteins that interrupt the immune process involved in psoriasis. Unlike generalized immunosuppressant therapies such as methotrexate, biologics focus on specific aspects of the immune function leading to psoriasis. In one embodiment compounds of this invention are used with a treatment involving interleukin antagonists. In one embodiment compounds of this invention are used with a treatment involving Ustekinumab (IL-12 and IL-23 blocker) or XP-828-L.

In one embodiment, antibiotics are employed when an infection, such as that caused by the bacteria *streptococcus* triggers an outbreak of psoriasis, as in certain cases of guttate psoriasis. According to this aspect of the invention, compounds of the invention are used as part of an overall treatment including antibiotics.

In one embodiment, compounds of this invention are used with climatotherapy which involves the notion that some diseases can be successfully treated by living in a particular climate. Several psoriasis clinics are located throughout the world. The dead sea is one of the most popular locations for climotherapy that can be used together with compounds of this invention.

In one embodiment, compounds of this invention are used with doctor fish which live in the outdoor pools of spas, and which are encouraged to feed on the psoriatic skin of people with psoriasis. The fish only consume the affected areas of the skin. The outdoor location of the spa may also have a beneficial effect on the condition of the subjects. This treatment can provide temporary relief of symptoms.

In one embodiment, compounds of this invention are used while patients are exposed to sun and sea water. In one embodiment, compounds of this invention are used with herbology as a holistic approach that aims to treat the underlying causes of psoriasis. In one embodiment, compounds of this invention are used with alternative therapies introducing oil of oregano as a powerful herbal method of treatment.

In one embodiment, compounds of this invention are used in combination with psychological symptom management program.

In one embodiment, Zinc oxide (ZnO) is used in combination with treatment involving compounds of this invention.

Preparation and Characterization of Compounds

In some embodiments, through the use of various chain lengths, side chains, and side chain terminal groups, great flexibility in compound chemical composition, size, structure, and function can be obtained. In some embodiments, such compounds may be constructed via multiple-step reaction pathways that involve synthesis of a suitable starting material or intermediate with a protected functional group prior to a synthesis step, followed by deprotection. In other embodiments, the synthesis may be carried out with a chemical/enzymatic/chemo-enzymatic approach, based on natural precursors.

Synthesis of the compound precursors of this invention may be carried out in a number of representative suitable solvents including anhydrous polar aprotic solvents such as acetonitrile, tetrahydrofuran, dioxane, or the like, halogenated solvents such as chloroform, or the like, solvents like methanol, ethanol and the like. In some embodiments, synthesis is conducted as exemplified herein, or as a variation thereof, as will be appreciated by the skilled artisan.

In one embodiment, OH groups representing the X, Y and Z moieties on the compound of formula I, are substituted with poly unsaturated fatty acid (PUFA) or derivatives of PUFA's. In one embodiment, PUFA's provide beneficial effects in the treatment of proliferative diseases. In one embodiment, PUFA's provide beneficial effects in the treatment of psoriasis. In one embodiment, PUFA's play a role in the reduction of markers of immune cell function. In one embodiment, the PUFA is linolenic acid or γ-linolenic acid.

Compounds obtained by methods as described herein can be characterized by methods well known in the art. For example, the molecular weight can be determined by various mass spectrometry techniques. Physical and thermal properties of the compounds can be evaluated by UV/vis and IR spectroscopies and chromatography. The chemical structures of the compounds can be determined by, e.g., NMR (1H, 13C NMR, 1H-1H correlation, or 1H-13C correlation), IR, UV, Gas Chromatography-Electron Impact Mass Spectroscopy (GC-EIMS), EIMS, or Liquid Chromatography Mass Spectroscopy (LCMS). Melting point and miscibility experiments can further characterize the compounds of this invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

EXAMPLES

The following examples are presented in order to more fully illustrate some embodiments of the invention. They should, in no way be construed, however, as limiting the scope of the invention.

Materials and Methods

Synthesis of Calcipotriol Derivatives

Oxidation process over the calcipotriol using various reagents was carried out to obtain a series of potential anticancer analogs derived from calcipotriol. Purification process to the crude material was performed by flash chromatography (MPLC). Purity was measured by HPLC and structure elucidation was carried out using NMR, MS (ESI-MS; GC-MS) and IR. Calci-dioxole (BGP-13) was obtained by reacting calcipotriol with O2, in the presence of methylene blue, in methanol and RT according to the following scheme:

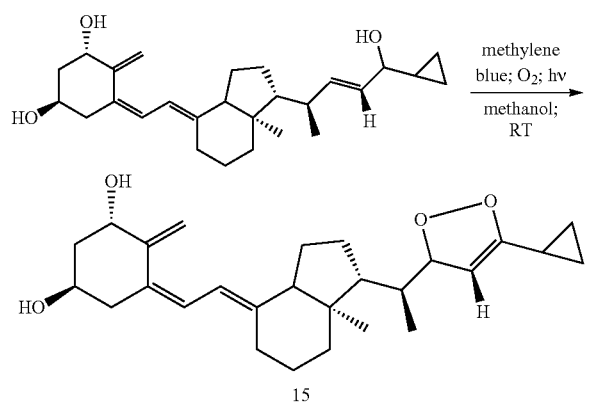

Calci-Cl BGP-15) was synthesized by reacting calcipotriol with HCl and O2, in ethanol/RT according to the following scheme:

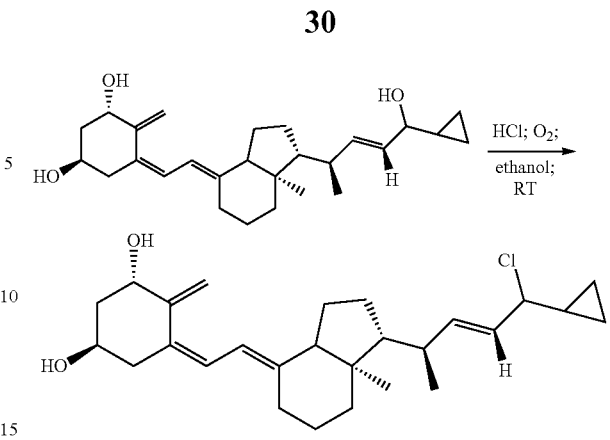

Cell culture: The following human cell lines (1) LNCaP—human prostate carcinoma cell line (2) MCF-7—human breast carcinoma cell line, and (3) GA—human melanoma cell line (3) HaCaT—immortalizes normal human skin keratinocytes were tested. Cells were inoculated in RPMI 1640 (LNCaP and GA) or Dulbecco modified eagle medium-DMEM (MCF-7 and HaCaT) supplemented with 10% heat inactivated fetal calf serum, 200 µM L-glutamine, 10 units/ml Penicillin and 10 µgr/ml Streptomycin. The cells were kept at 37° C. in a 5% $CO_2$ humidified atmosphere.

FACS Analysis

The population of cells undergoing apoptosis and its cell-cycle stage was evaluated by flow cytometry. Cells ($0.4 \times 10^6$) were treated with the different substances for 4-5 days as previously described. The cells were then collected along with extracellular medium—in order to collect disconnected cells, and washed with cold PBS. The samples were fixated in 70% ethanol at −20° C. for 24-48 h. Cells pellets were then washed in cold PBS and suspended in PBS containing 0.1% Triton-X and 30 mg/ml RNAase (DNAase free) A for 6 h in room temperature. Approximately one minute before the cells were analyzed by flow cytometry, 3 µl propidium iodide (2 mg/ml) were added and then analyzed.

Western Blot Analysis

Cells were incubated for 5 minutes at room temperature in 100 µl of 1% SDS lysis buffer. Samples were then collected into eppendorfs, incubated for 10 minutes at 100° C., and centrifuged at 14,000 rpm for 10 minutes. Supernatants were transferred into new tubes and pellets were discarded. Determination of protein concentration was conducted using the Bradford assay. 75 mg protein of each sample was loaded on PVDF membranes and incubated with anti p21 antibody (Santa Cruz Biotechnology, Santa Cruz, Calif., U.S.A).

Example 1

The Compounds of This Invention Exhibit Potent Antiproliferative Activity

The direct effect of the compound compared to free calcipotriene and vitamin $D_3$ in the viability and proliferation level of cultured cells was assessed in vitro using cultured Cells. The cells were inoculated in 0.2 ml fresh medium. After 24 at 37° C. in a 5% $CO_2$ humidified atmosphere, the medium was replaced with a fresh medium containing 0.5% ethanol and 30, 5, 1 and 0.1 µM test substance. Medium containing 0.5% ethanol without test compounds was used for the control cells. Cell growth and proliferation was assayed by Neutral-Red assay (evaluated by measuring the absorbance of the dye following 3 hours incubation, in 540 nm) at the stated times.

Figure 1B:
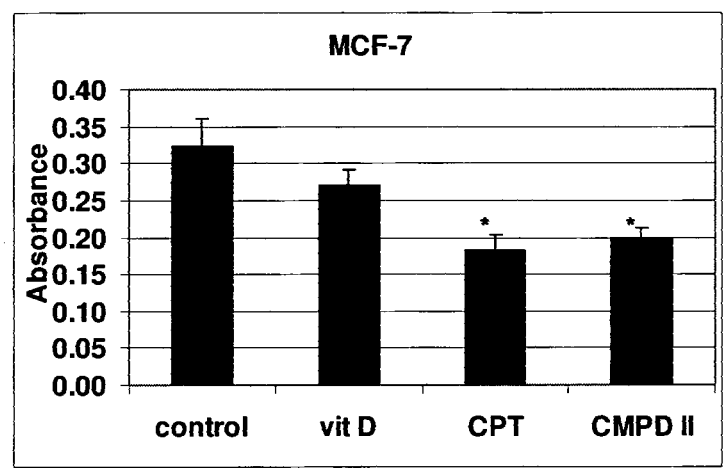
Figure 1C:
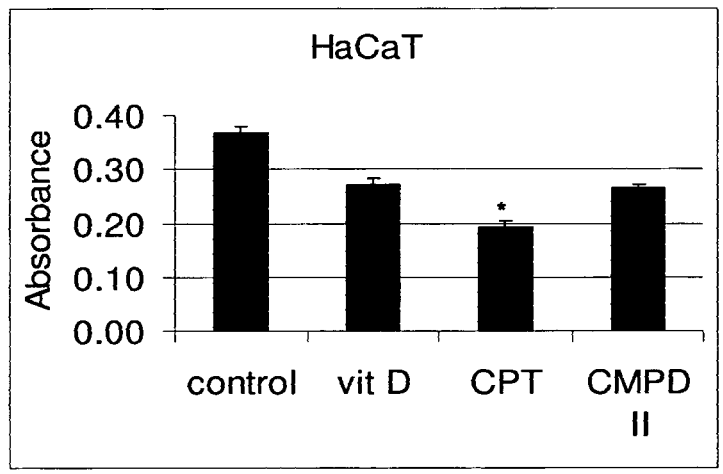
Figure 2A:
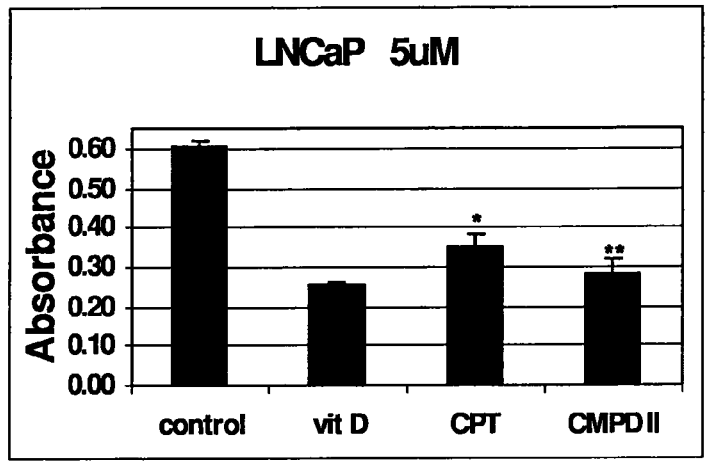
FIG. 2 depicts the results of a viability assay in LNCaP cell lines following 5 μM, 1 μM and 100 nM treatments, with calcitriol (vit D); calcipotriol (CPT) and Compound II for 6 days. LNCaP cells exposed to 5 μM Compound II for 6 days showed higher mortality than cells exposed to calcipotriol alone. Cells exposed to 1 μM and 100 nM Compound II for 6 days showed similar mortality to cells exposed to calcitriol and calcipotriol alone.
Figure 2B:
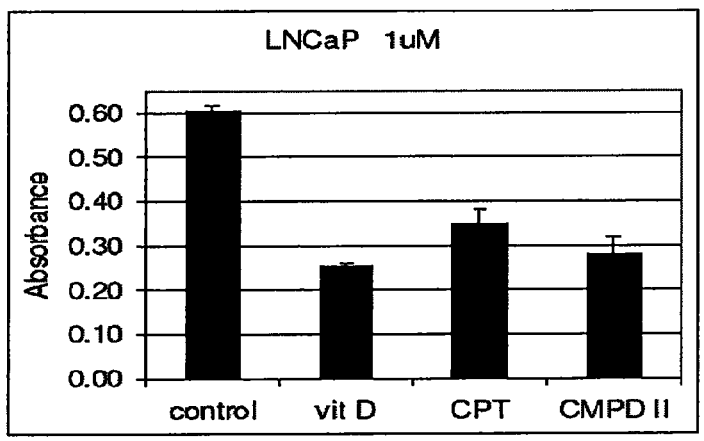
Figure 2C:
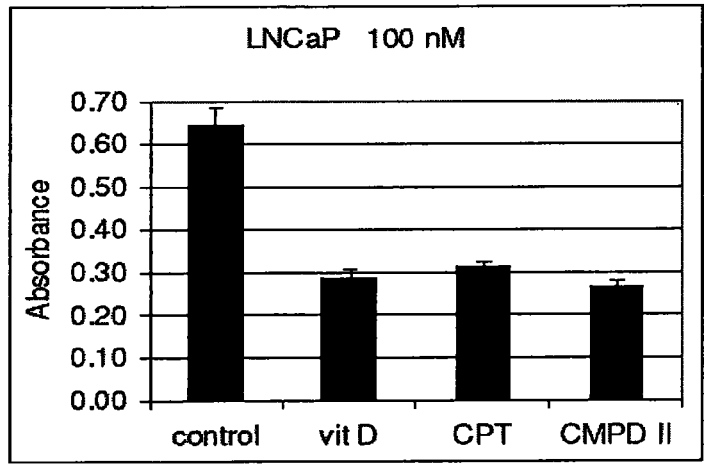

FIG. 1 shows that Compound II has a much more potent antiproliferative effect on the LNCaP and MCF-7 cancer cells as compared to HaCaT cells. Moreover, BGP-13 has a much more potent antiproliferative effect on LNCaP cells than calcipotriol alone.

Figure 3A:
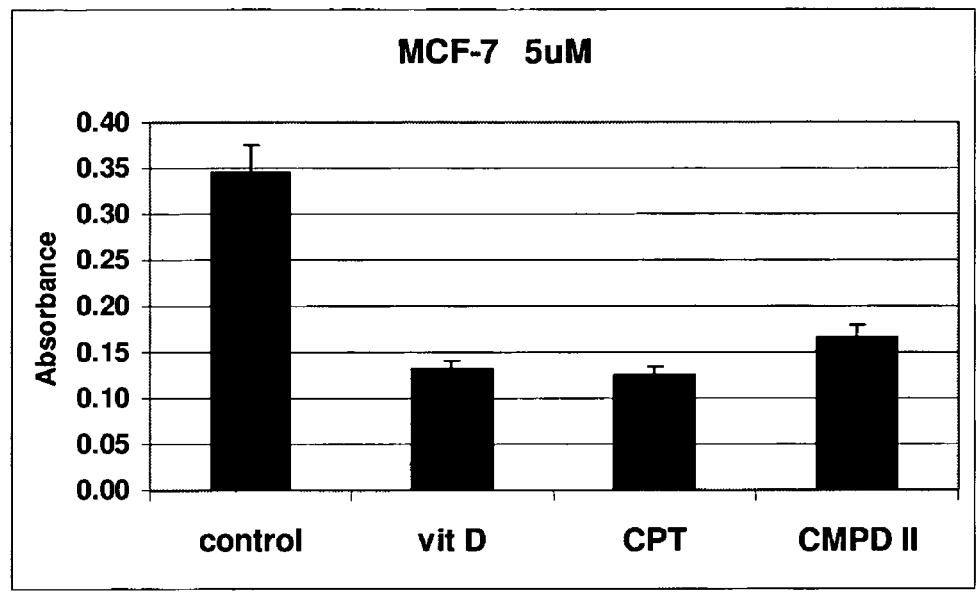
FIG. 3 depicts the results of a viability assay in MCF-7 cell lines following 5 μM, 1 μM and 100 nM treatments, with calcitriol (vit D); calcipotriol (CPT) and Compound II for 6 days. Treatment with 5 μM, 1 μM and 100 nM Compound II for 6 days has a similar potent antiproliferative effect on MCF-7 cells as treatments with calcitriol and calcipotriol.
Figure 3B:
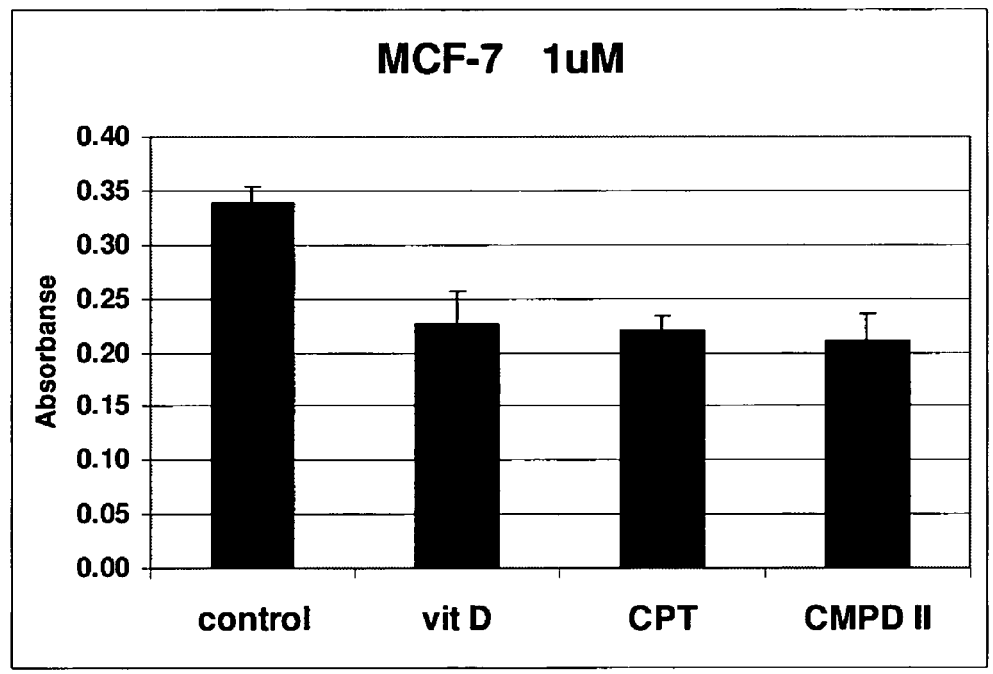
Figure 3C:
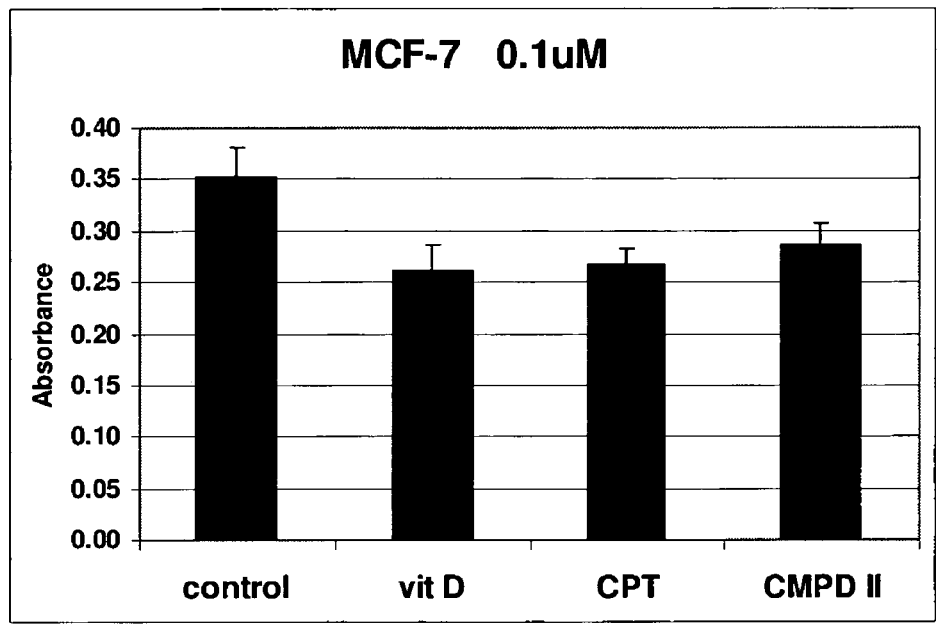
Figure 4:
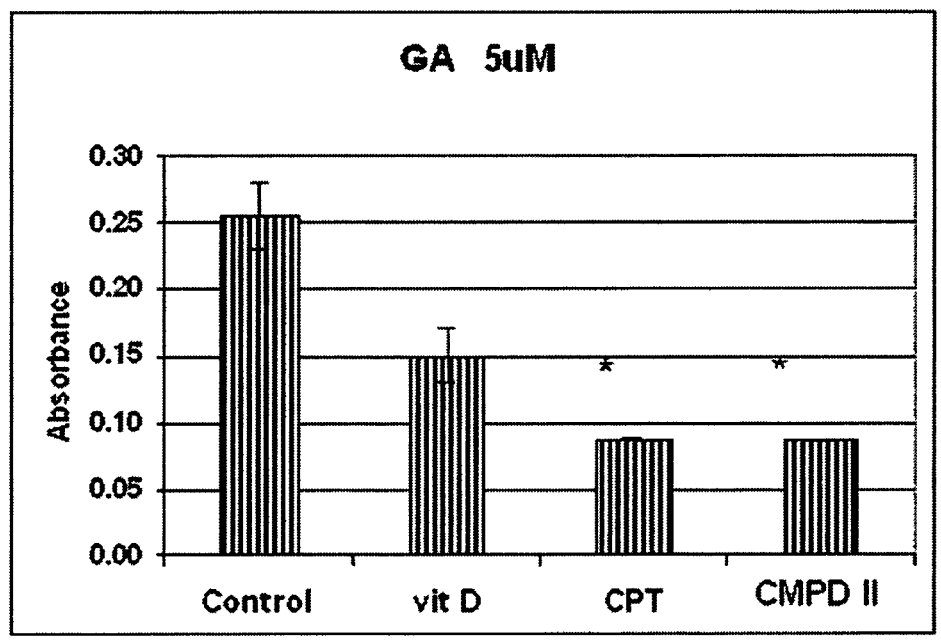
FIG. 4 depicts the results of a viability assay in GA cells following 5 μM treatments, with calcitriol (vit D); calcipotriol (CPT) and Compound II for 6 days. The plot show a preliminary result obtained from one assay. GA cells exposed to 5 μM Compound II for 6 days showed similar mortality as cells exposed to calcipotriol alone, and more significant than treatment with calcitriol alone.

In viability assays conducted in LNCaP (A), MCF-7 (B) and HaCaT (D) cell lines following 5 μM, 1 μM and 100 nM treatments and GA (C) cells following 5 μM treatments, with calcitriol (vit D); calcipotriol (CPT) and Compound II for 6 days, LNCaP cells exposed to 5 μM Compound II for 6 days showed higher mortality than cells exposed to calcipotriol alone. Cells exposed to 1 μM and 100 nM Compound II for 6 days showed similar mortality to cells exposed to calcitriol and calcipotriol alone. FIG. 3 shows that treatment with various dosages of Compound II for 6 days has a similar potent antiproliferative effect on MCF-7 cells as treatments with calcitriol and calcipotriol. FIG. 4 shows that GA cells exposed to 5 μM of Compound II for 6 days showed similar mortality as cells exposed to calcipotriol alone, and more significant than treatment with calcitriol alone [asterisk notes $p<0.001$ relative to vitamin $D_3$].

Figure 5A:
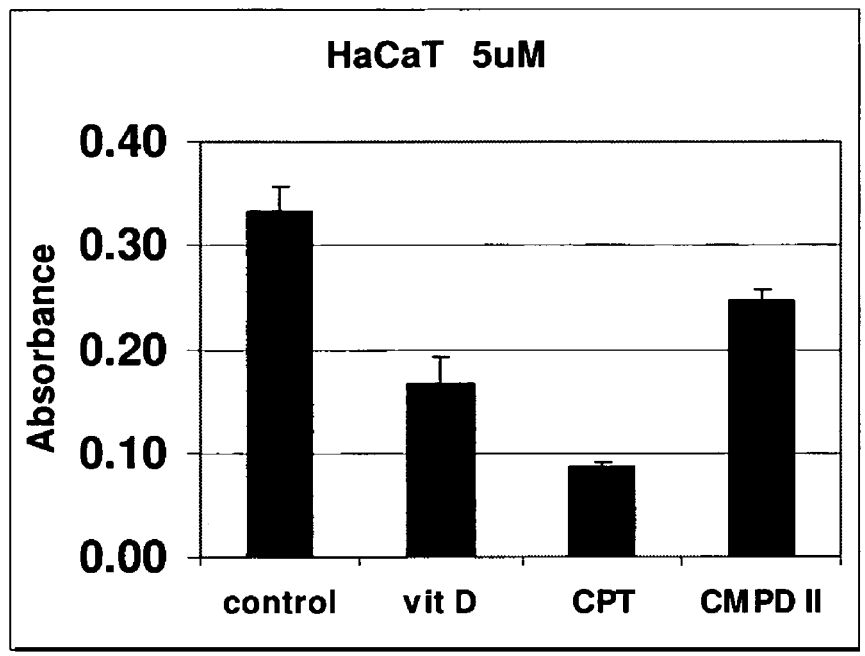
FIG. 5 depicts the results of a viability assay in HaCaT cell lines following 5 μM, 1 μM and 100 nM treatments, with calcitriol (vit D); calcipotriol (CPT) and Compound II for 6 days. Treatment of HaCaT cells with 5 μM and 1 μM Compound II for 6 days is less potent than treatments with calcitriol and calcipotriol. This resembles the result shown in FIG. 1 and indicates that Compound II might have a less potent effect on non-carcinogenic cells than on carcinogenic cells.
Figure 5B:
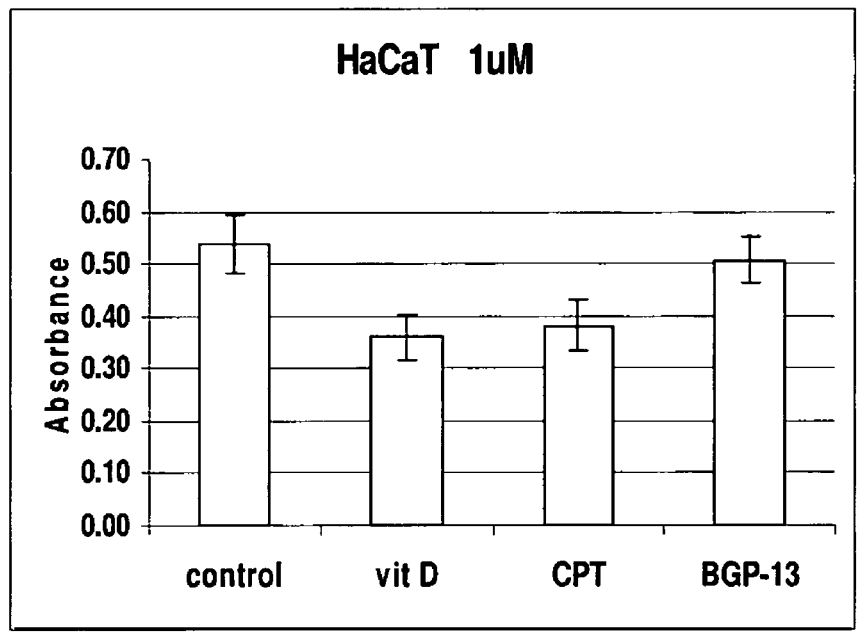
Figure 5C:
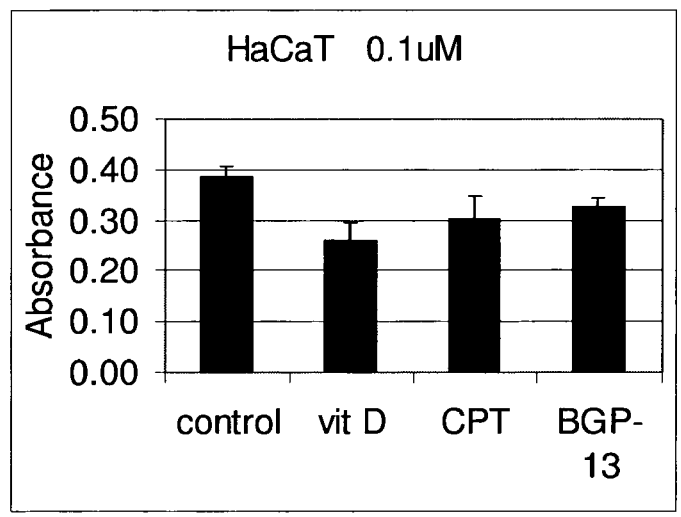

FIG. 5 shows that treatment of HaCaT cells with 5 μM and 1 μM Compound H for 6 days is less potent than treatments with calcitriol and calcipotriol, thus the effect of Compound II is more selective for carcinogenic cells.

Figure 6A:
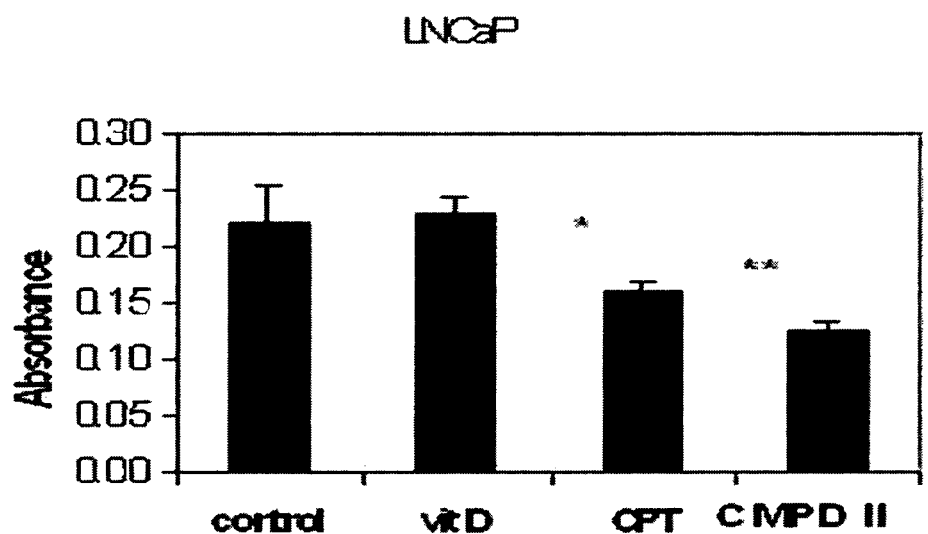
FIG. 6 depicts the effect of Compound II on LNCaP cell line. A significantly high efficacy of Compound II substance against human cancer cell lines (Prostate cancer (LNCaP)) was shown in-vitro, while it's related drug substances, calcitriol (1,25-di-OH vit D3) and calcipotriol (FIG. 6A) had a relatively lower anticancer effect.
Figure 6B:
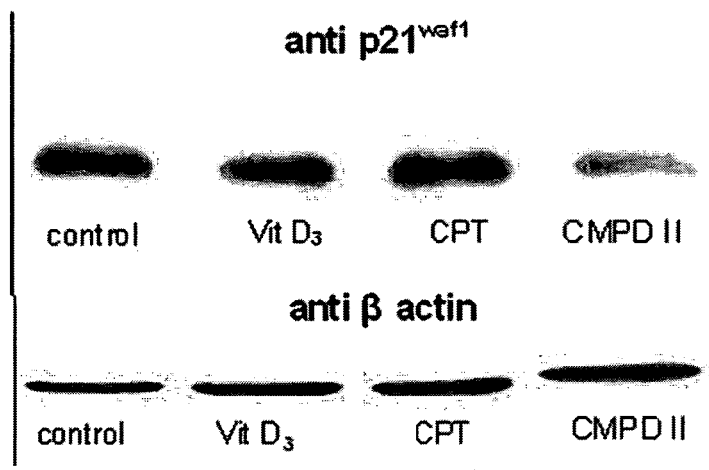

FIG. 6A shows a significantly high efficacy for Compound II against human cancer cell lines (Prostate cancer (LNCaP) in-vitro, while the structurally related calcitriol (1,25-di-OH vit D3) and calcipotriol were less efficacious. The antiproliferative effect of Compound II on different human cancer cell lines was not mediated through increased p21 expression, in contrary to calcitriol and calcipotriol (FIG. 6B).

Figure 7:
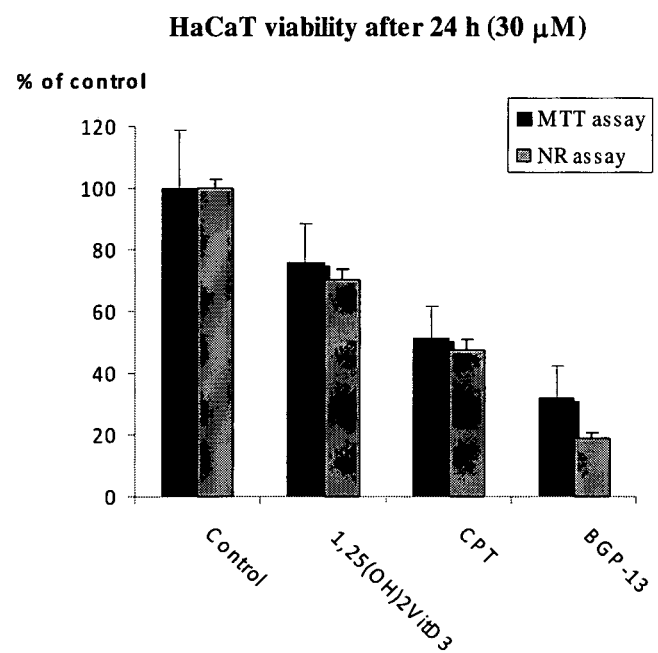
FIG. 7 is a bar graph showing the results of a MTT and NR viability assays for HaCaT cells treated with 30 82 M (for 24 hours) of 1α,25(OH)2 vitamin D3, calcipotriol (CPT), and BGP-13.

Viability of HaCaT cells in the presence of three vitamin D3 derivatives, 1α,25(OH)2 D3 (calcitriol), and BGP-013 was studied by MTT assay. The results showed that BGP-13 inhibited the proliferation of the keratinocytes at the same rate and extent as CPT or calcitriol (FIG. 7). A similar anti-proliferative effect was noted using human dermal fibroblasts.

Morphology studies revealed an increase in the cancer cell size suggesting a non-apoptotic death pathway. Preliminary metabolic studies showed that the compounds were able to stay stable and to cross the cell membrane to the cytosolic part. A preliminary toxicological test in rats showed that the compound is not toxic up to 5 mg/kg.

Example 2

Cellular Entry

Figure 8A:
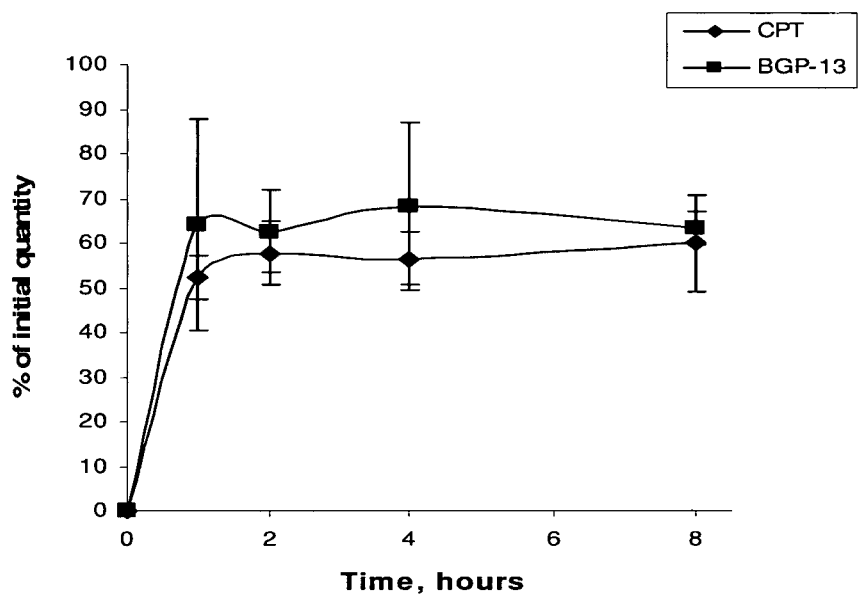
FIG. 8 is a representative of two experiments. 6A. Cells exposed to 30 μM of calcitriol (vit D); calcipotriol (CPT) and Compound II for 24 hours; and 6B. The p21$^{WAF1}$ expression in LNCaP cells after 48 hours of 100 nM. The antiproliferative effect of Compound II on different human cancer cell lines was not mediated through increased p21 expression, in contrary to calcitriol and calcipotriol (FIG. 6B).
Figure 8B:
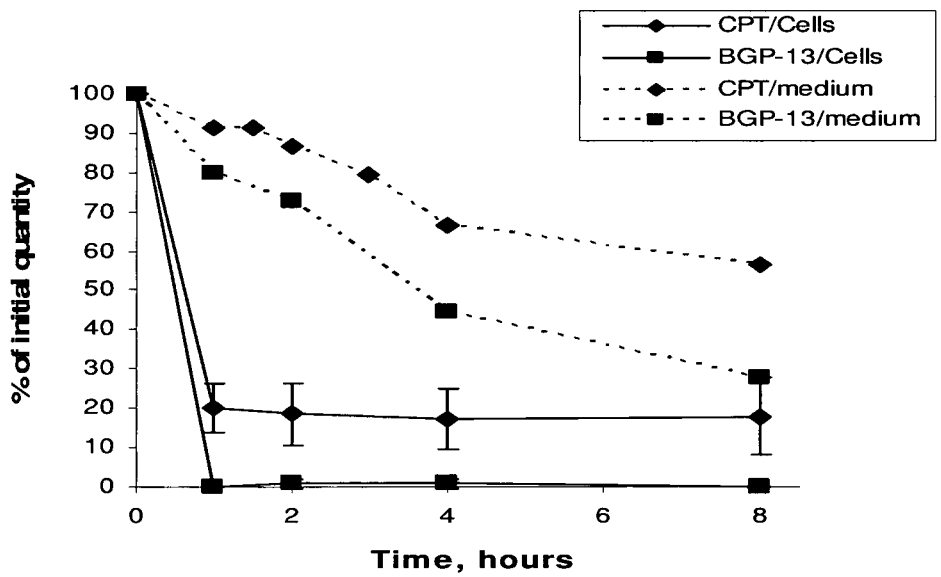
Figure 9:
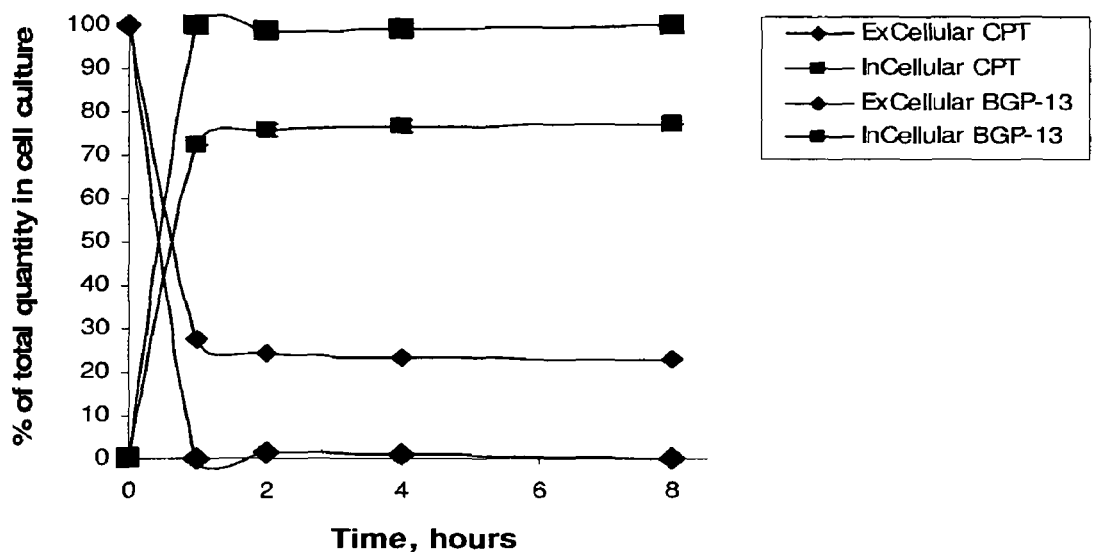
FIG. 9 is a graph showing cell internalization kinetics of BGP-13 and CPT as expressed by extracellular or intracellular fraction (in %) of the total quantity momentarily present in the cell culture at a specific time.

External and internal fractions of HaCaT cultures (0.5× $10^6$, $1 \times 10^6$, $3 \times 10^6$, $5 \times 10^6$ and $9.7 \times 10^6$ cells) were analyzed by HPLC. The entry of BGP-13 into keratinocytes was approximately 60% of the applied substance and comparable to CPT (FIG. 8a), even though the derivative (BGP-13) was significantly less stable in the medium relative to CPT (FIG. 8b). When calculating the fractions penetrated as fractions of the total quantity momentarily present in the cell culture at any specific time, it was actually demonstrated that BGP-13's enhanced intracellular permeation increased its stability by preventing degradation in the medium (FIG. 9). It should be noted that the cell internalization of both CPT and BGP-13 as normalized per cell was found to be constant even at a high cell density (data not shown), implying an active transport mechanism.

Example 3

Biotransformation of CPT to BGP-13

Figure 10A:
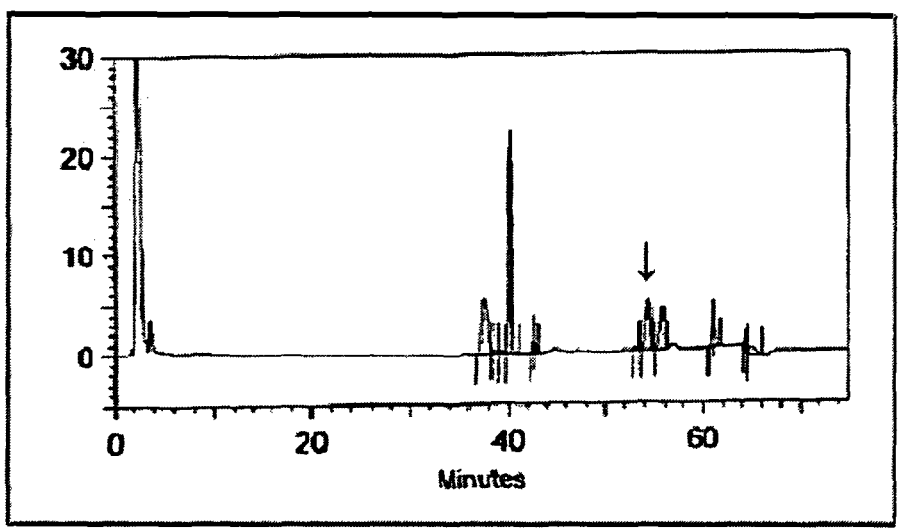
FIG. 10 are graphs showing LC-MS spectral analysis of the metabolite peak of calcipotriol relating to BGP-13.
Figure 10B:
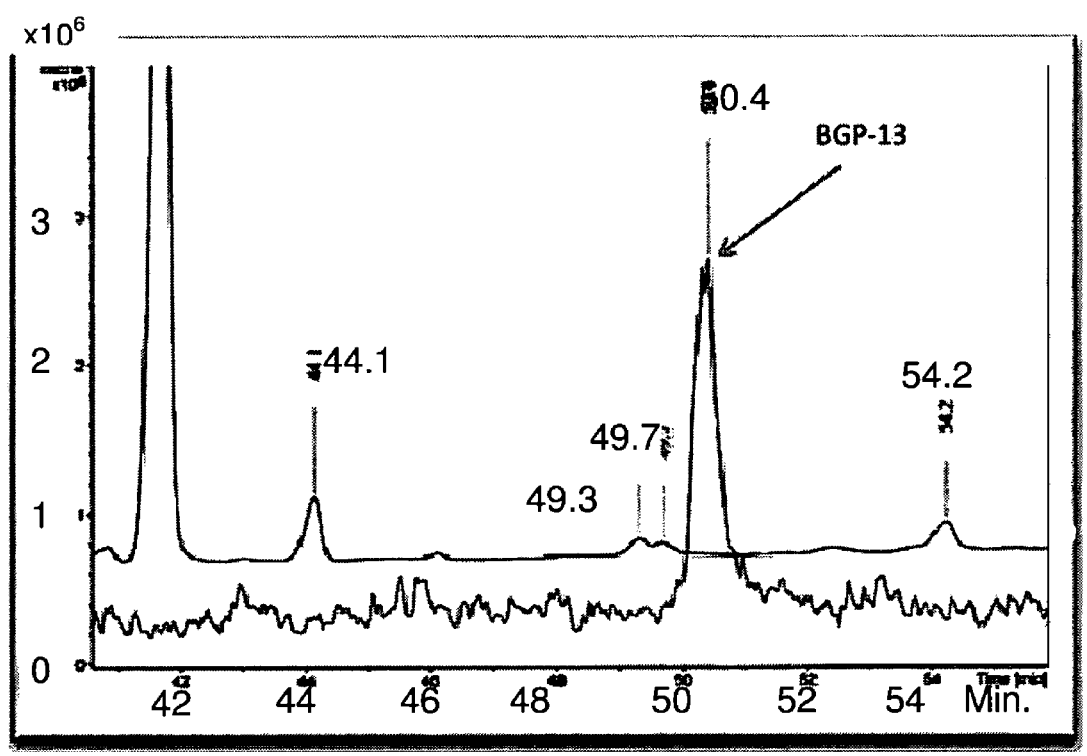
Figure 10C:
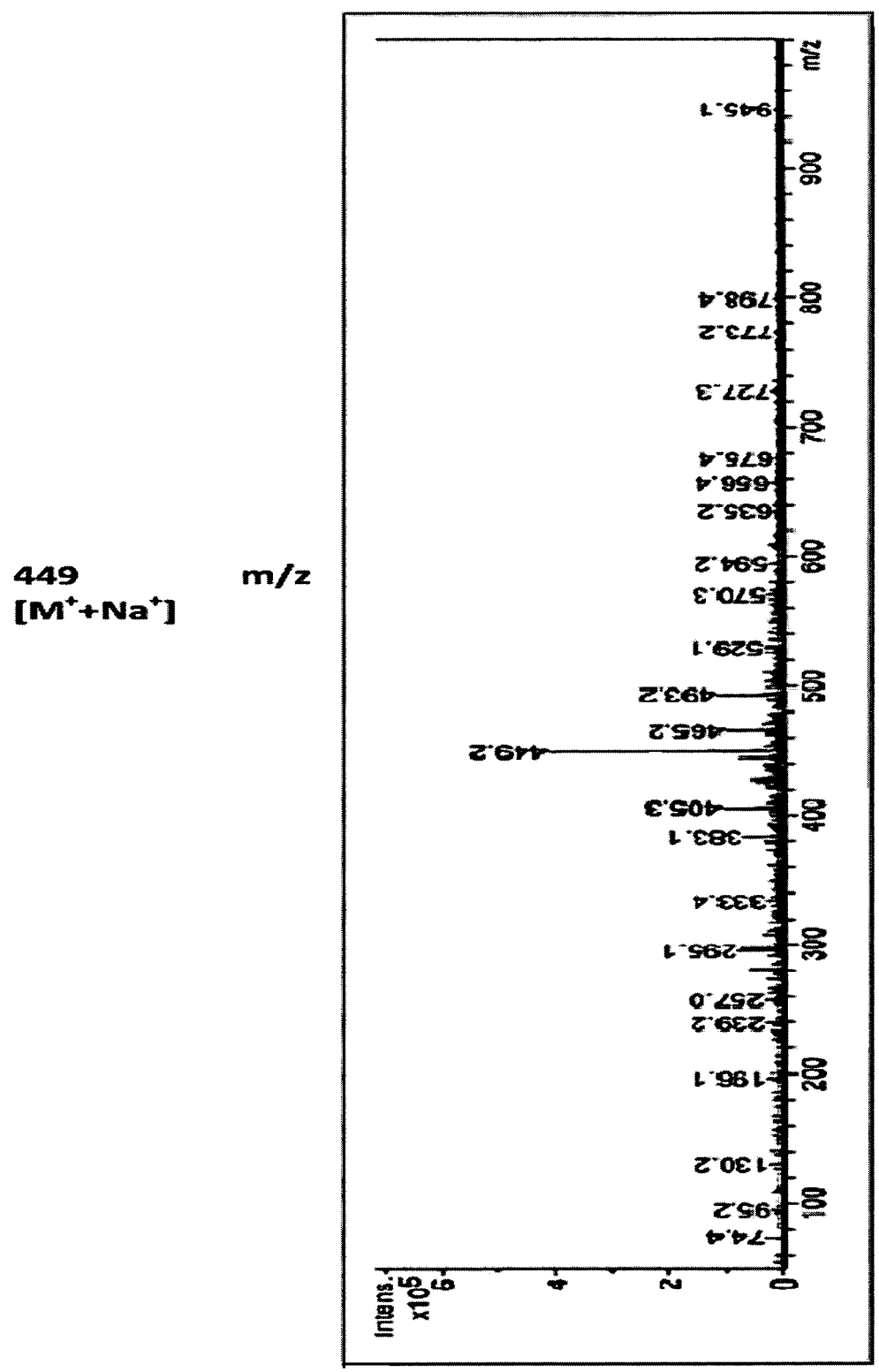

BGP-13 is a natural metabolite of CPT while it had been detected by HPLC in the intracellular fraction of keratinocytes following 4 hour incubation of HaCaT cells with CPT. LC/MS analysis has confirmed that the metabolite peak appeared at BGP-13's retention time was indeed this derivative (FIG. 10). BGP-13 was also found at low levels as a natural CPT metabolite in rat skin. The formation of reduced levels of this metabolite is probably due to the poor penetration of calcipotriol into the skin. Therefore, intracellular BGP-13 is an enzymatic product of the internalized CPT with reactive oxygen species (ROS) such as singlet oxygen. This metabolic pathway of calcipotriol may have a role in scavenging ROS and reducing inflammatory processes in cells and tissue.

Figure 11:
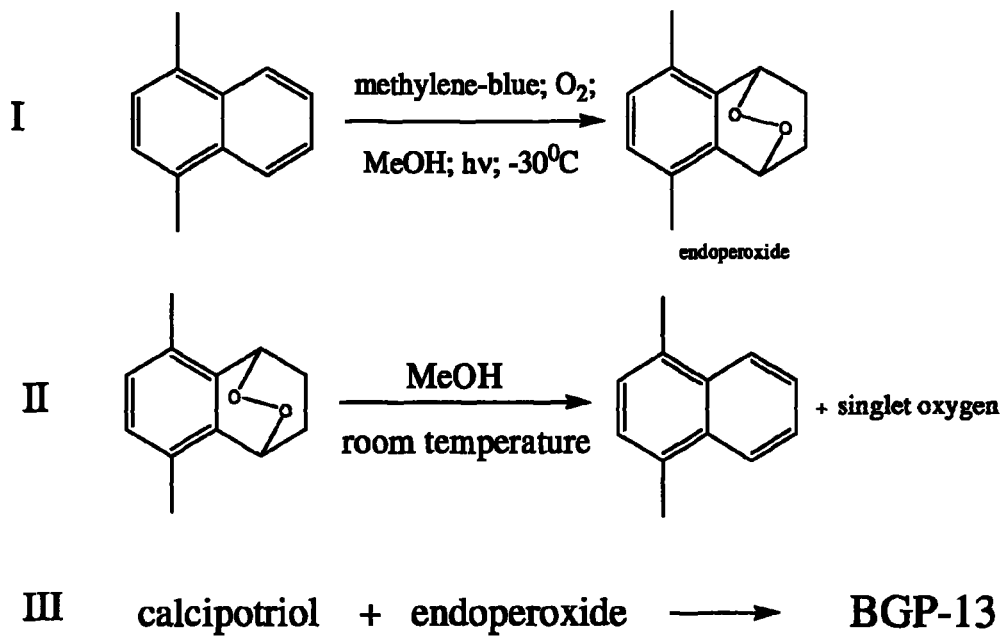
FIG. 11 is a chemical reaction scheme showing the involvement of singlet oxygen in the reaction leading to BGP-13 production.
Figure 12A:
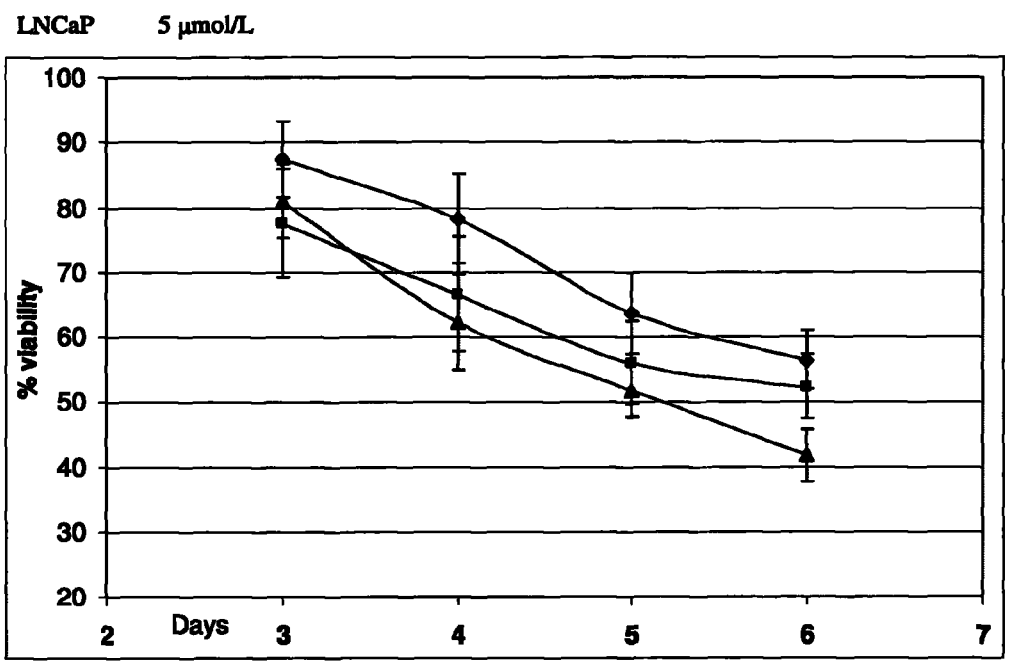
FIG. 12 are graphs showing that Vitamin $D_3$, calcipotriol and BGP-15 reduce prostate and breast cancer cells survival. LNCaP and MCF-7 cells were plated in 96-well plates and treated with 1 or 5 μmol/L test substances for 3 to 6 days. Cell viability following treatments was assayed by MTT. All experiments were conducted at least twice, and weighted results from all experiments are shown. *p<0.005 of BGP-15 relative to vitamin $D_3$, **p<0.001 of BGP-15 relative to vitamin $D_3$ and to calcipotriene.
Figure 12B:
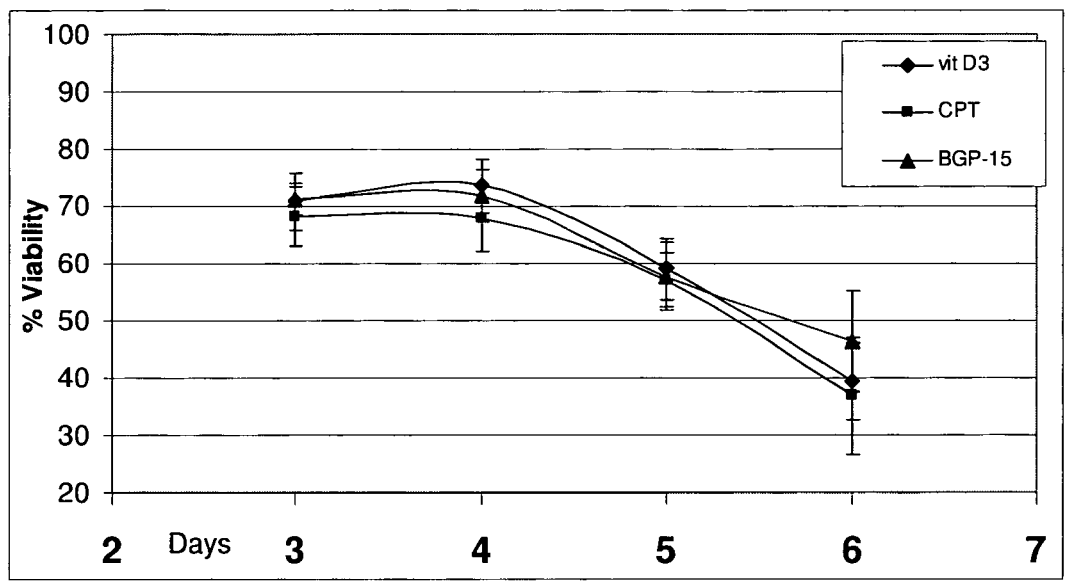
Figure 12C:
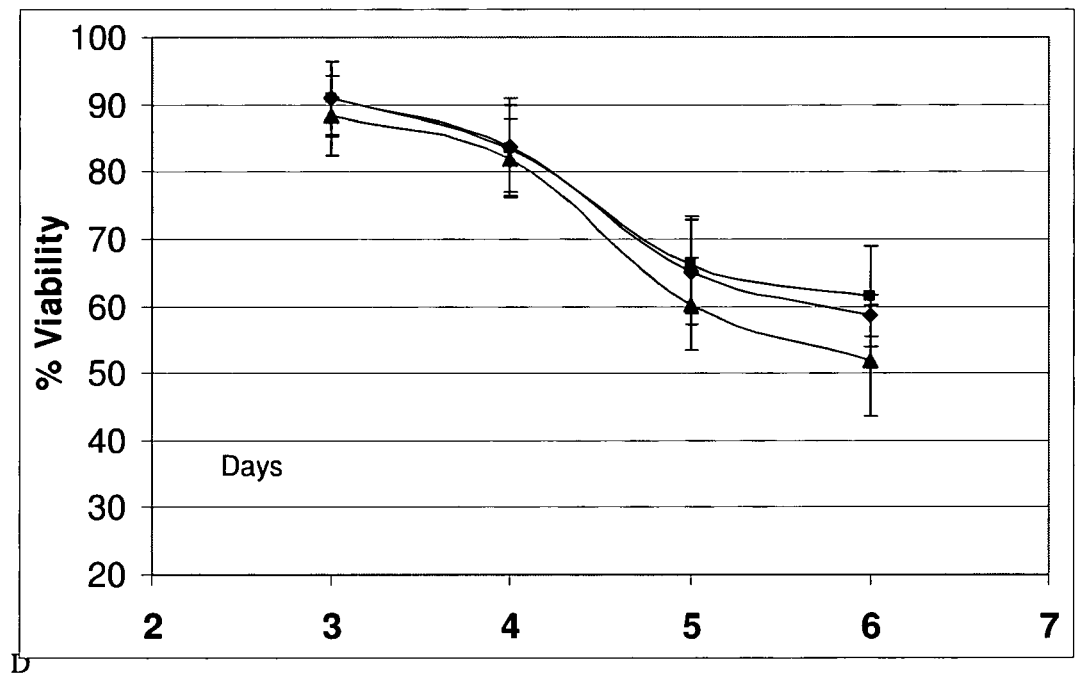
Figure 12D:
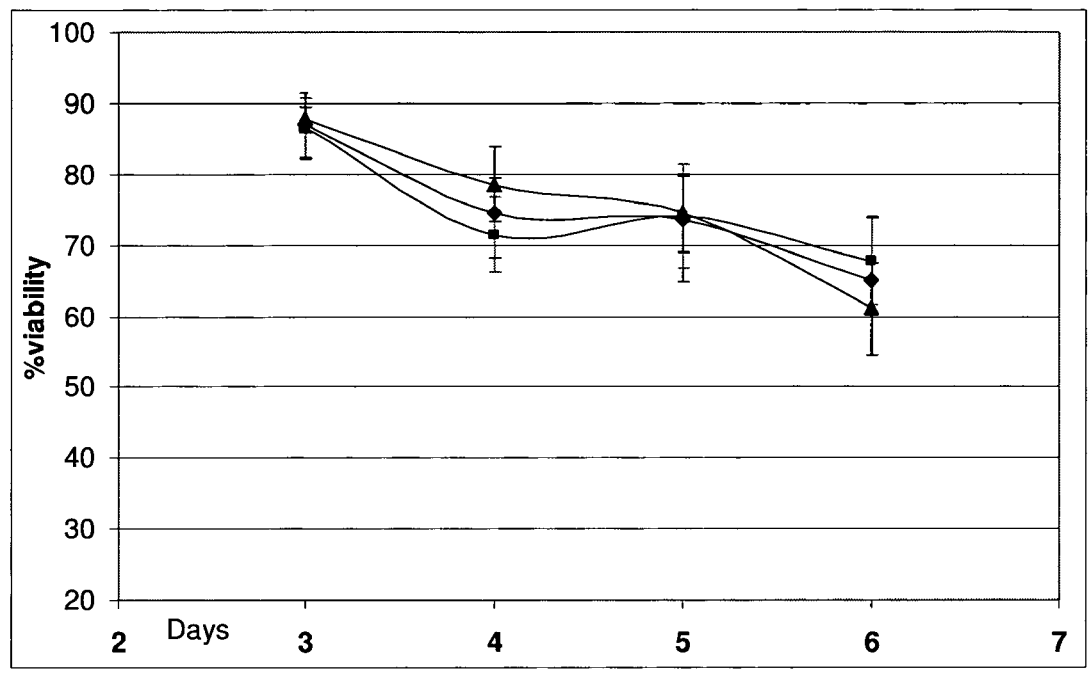

Reaction with singlet oxygen: To prove the involvement of singlet oxygen in the reaction producing BGP-13 and to understand the chemical reaction mechanism of BGP-13 in general, a singlet oxygen trapper was prepared. The trapper, endoperoxide-naphthalene, was converted into naphthalene and released exclusively singlet oxygen at room temperature (FIG. 11). Combining calcipotriol with the endoperoxide has created a new product that was first detected by TLC as BGP-13. LC-MS has confirmed that this indeed is the substance. It has been evidenced, therefore, that CPT acts in cells, at least in part, as an antioxidant/quencher of singlet oxygen.

Example 4

The Effect of Calcipotriene and BGP-15 on Prostate and Breast Carcinoma Cells Viability LNCaP and MCF-7 cell-lines are widely used models for human prostate and mammary carcinomas respectively. Following BGP-15 purification and structural elucidation (FIG. 12), the effect of calcipotriene and BGP-15 on the viability of both LNCaP and MCF-7 cells was tested in-vitro by using the MTT assay, and was compared with the effect obtained by vitamin D3 (calcitriol).

Figure 13:
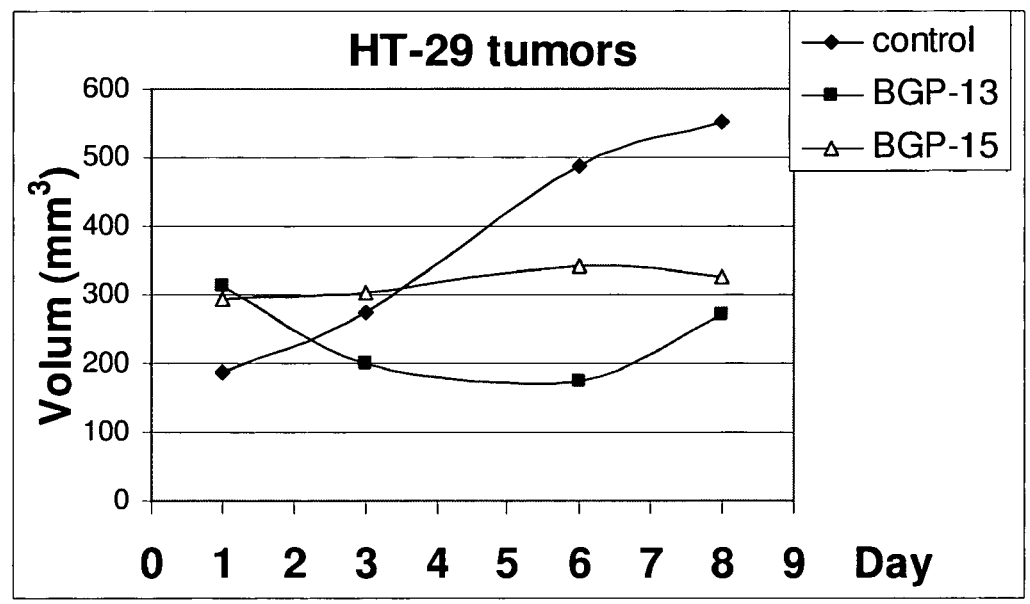
FIG. 13 is a graph showing results of in vivo action of BGP-13 and BGP-15 on HT-29 cancer growth.
Figure 14:
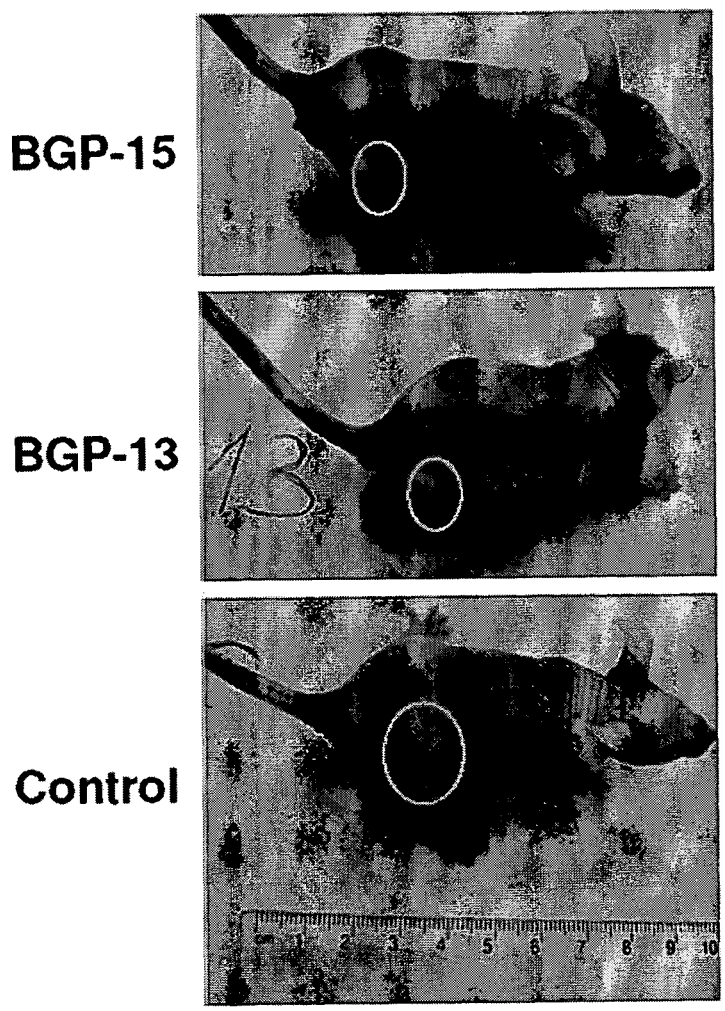
FIG. 14 are photos showing the effect of 2 μg/kg dose of BGP-13 and BGP-15 (ip) in vivo.

In vivo anti-tumor activity of the novel derivatives of calcipotriol: Experiments were carried out to determine the ability of BGP-13 and BGP-15 to inhibit the growth of human tumor cells in vivo. BGP-13 and BGP-15 were chosen for the in vivo assays since they were active at least against three cell lines of human origin (HT-29, MCF-7, and LNCaP). Nude mice received a subcutaneous (sc) injection of HT-29 human colon cancer cells. At various time intervals after the administration of the tumor cells, the mice received three times per week intraperitoneal injections of BGP-13 and BGP-15 at a dose of 2 μg/kg. Treatment of mice with BGP-13 and BGP-15 at a dose of 2 μg/kg did not cause either weight loss or any observable adverse effects in the treated mice. In one experiment 12 nude mice, which received a s.c. injection of HT-29, were divided into three groups. Starting from day 20 after tumor injection, 2 groups of the mice received ip injections of BGP-13 and BGP-15 respectively. The size of tumors was significantly smaller in mice injected with BGP-13 and BGP-15 than in vehicle-treated control mice (FIG. 13). At 30 days after cancer cell injection, the tumors in the treated group were half the size of the tumors in controls (FIG. 14).

Example 5

Calcium Metabolic Model and Calcium Measurements

Figure 15:
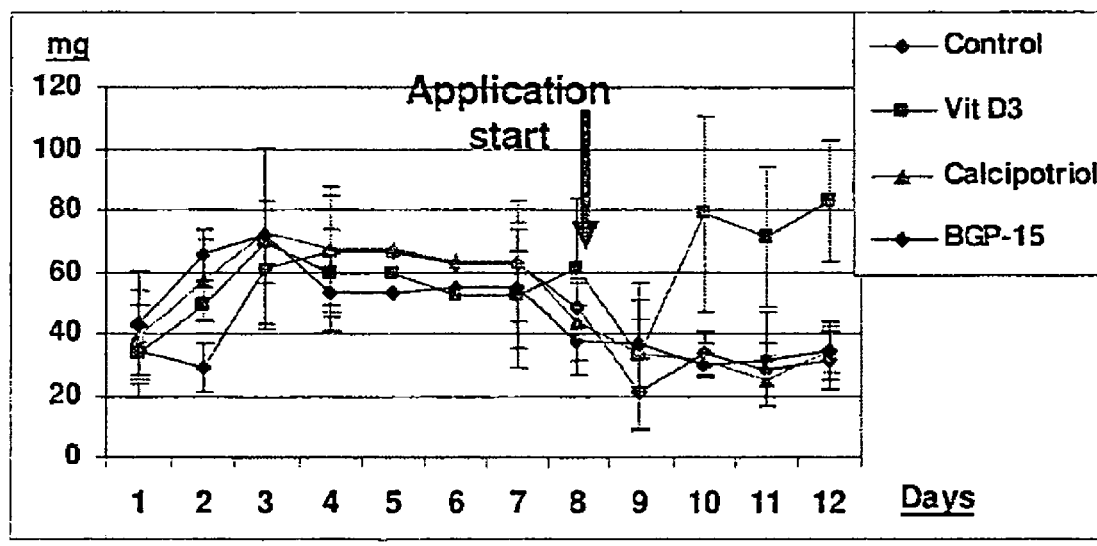
FIG. 15 is a graph showing quantification of urine calcium after BGP-15, vitamin D3 and CPT.

Treatments with calcipotriene and BGP-15 do not generate hypercalcemia or hypercalciuria in rats. The clinical use of vitamin D3 as an anti-cancer agent is limited by its toxicity and concerns the possible development of hypercalcemia or hypercalciuria in treated patients. The calcium levels in rat blood, and the total daily secretion of calcium in rat urine were evaluated following daily treatments of 20 ng of vitamin D3, calcipotriene or BGP-15 for six days as shown in FIG. 15.

What is claimed is:

1. A compound of formula I:

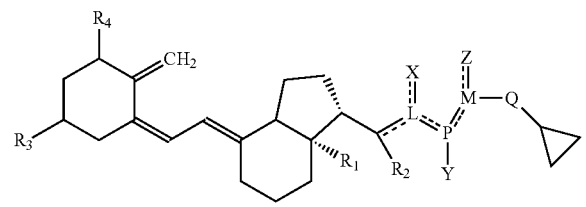

Formula I wherein: $R_1$ and $R_2$ are independently H, $C_{(1-4)}$ alkyl, halogen, cycloalkyl;
$R_3$ and $R_4$ are independently OH, OAlk, Alk denoting a $C_{(1-4)}$ alkyl group, halogen, CN, $NH_2$, $NO_2$, $C_{(1-4)}$ alkylene, haloalkyl;
L is carbon and optionally forms a double bond with P or with X, or L forms an epoxide with P;
P is carbon and optionally forms a double bond with L or M, or P forms an epoxide with L or M or P is O;
Q is nothing, or a carbonyl;
M is an alkylene ($C_1$-$C_4$), or optionally a carbon which forms a double bond with P, or M forms an epoxide with P;
Y is nothing, H, OH, OAlk, Alk denoting a $C_{(1-4)}$ alkyl group, O—CO-alkyl;
X is oxo, OH, or halogen, OAlk, Alk denoting a $C_{(1-4)}$ alkyl group, O—CO-alkyl;
Z is H, oxo, OH or halogen, OAlk, Alk denoting a $C_{(1-4)}$ alkyl group, O—CO-alkyl;
Or L, P, M, Z and X forms a saturated or unsaturated 5-7 membered, carbocyclic or heterocyclic ring, wherein L, P, M are defined as above and X and Z are independently O, N, S or C.

2. The compound of claim 1, wherein said compound is characterized by the structure of formula II:

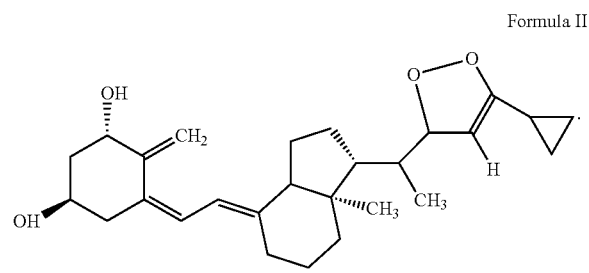

Formula II

3. A compound of formula III:

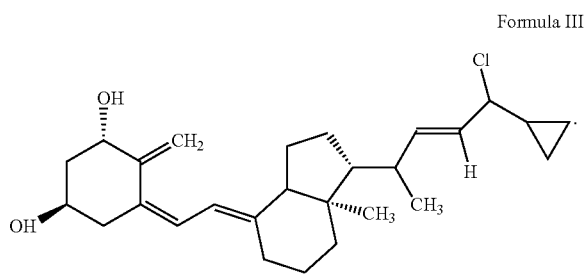

Formula III

4. The compound of claim 1, wherein said compound is characterized by the structure of formula IV:

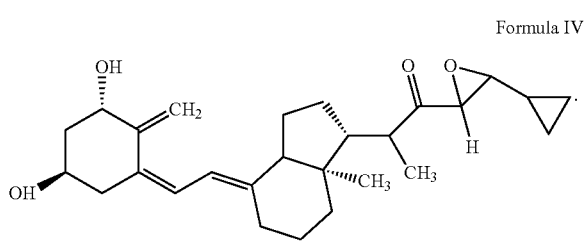

Formula IV

5. The compound of claim 1, wherein said compound is characterized by the structure of formula V:

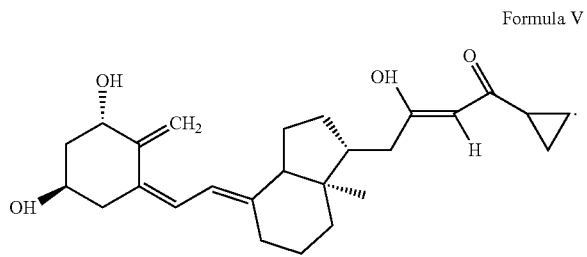

Formula V

6. The compound of claim 1, wherein said compound is characterized by the structure of formula VI:

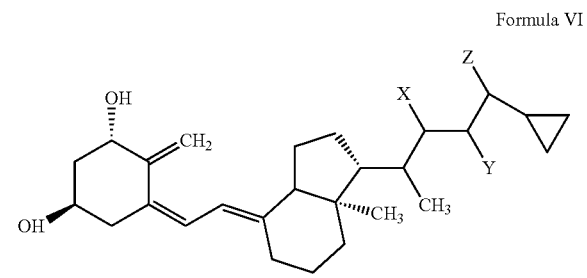

Formula VI wherein
Y and Z which may be the same or different, are H or OH or oxo groups; and
X is OH or oxo group.

7. The compound of claim 1, wherein said compound is characterized by the structure of formula VII:

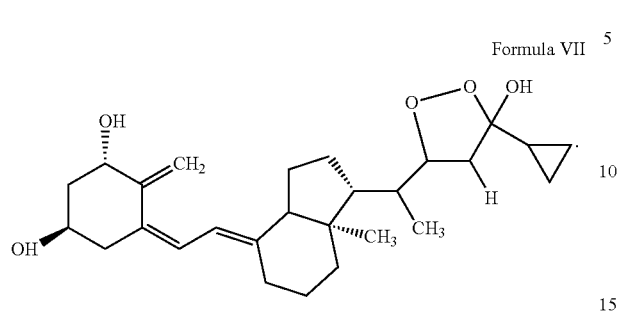

Formula VII

8. The compound of claim 1, wherein said compound is characterized by the structure of formula VIII:

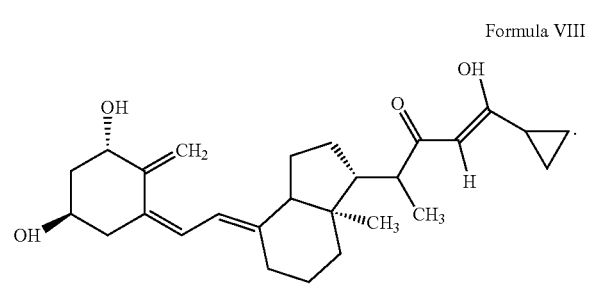

Formula VIII

9. A compound of formula IX:

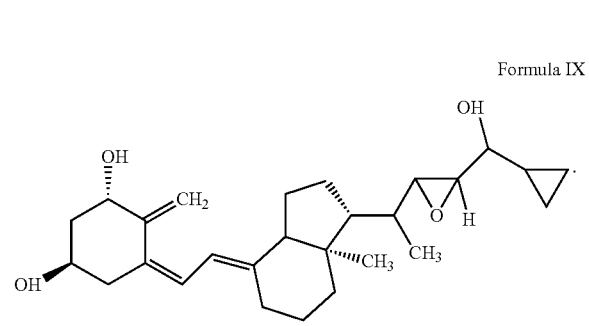

Formula IX

10. A compound of formula X:

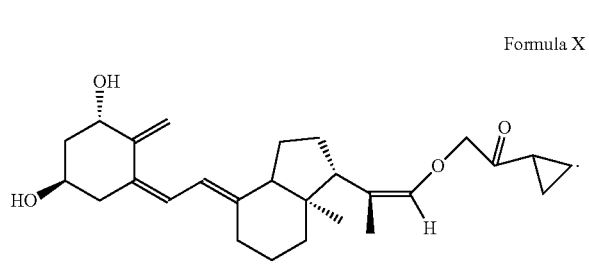

Formula X

11. A compound of formula XI:

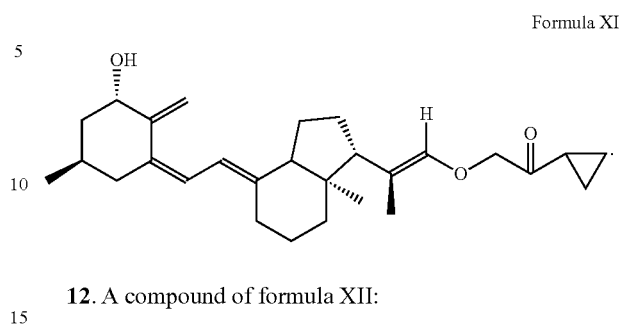

Formula XI

12. A compound of formula XII:

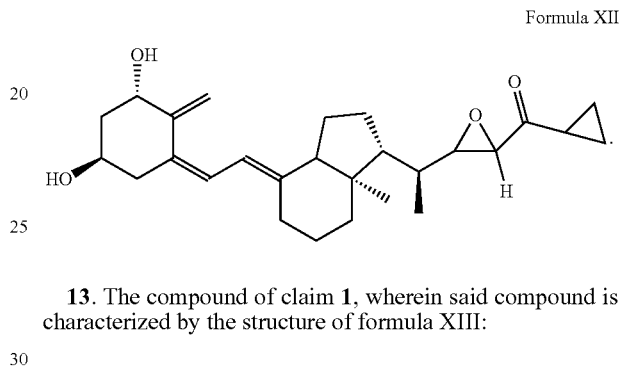

Formula XII

13. The compound of claim 1, wherein said compound is characterized by the structure of formula XIII:

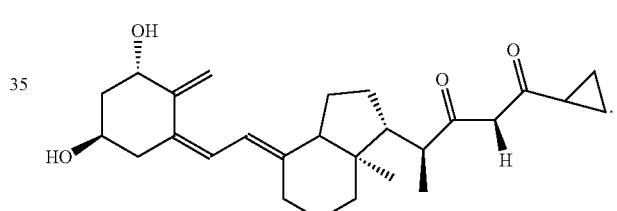

Formula XIII

14. A composition comprising the compound according to claim 1.

15. A method for treating, reducing incidence, delaying progression or pathogenesis, prolonging remission, inhibiting metastasis, or relieving the symptoms of a cancer in a subject having cancer, said method comprising administering to said subject a compound of claim 1, and wherein said cancer is colon, pancreatic, breast, or prostate cancer.

16. The method of claim 15, wherein said cancer is a carcinoma.

17. The method of claim 15, wherein the subject has precancerous precursors comprising an intraepithelial neoplasia.

18. The method of claim 15, further comprising administering an adjunct therapy to said subject.

19. The method of claim 18, wherein said adjunct therapy includes radiation, chemotherapy or immunotherapy.

20. A method for treating, reducing incidence, delaying progression or pathogenesis, or relieving the symptoms of psoriasis in a subject having psoriasis, said method comprising administering to said subject a compound of claim 1.

* * * * *